United States Patent
Kohli et al.

(10) Patent No.: US 11,538,560 B2
(45) Date of Patent: Dec. 27, 2022

(54) IMAGING RELATED CLINICAL CONTEXT APPARATUS AND ASSOCIATED METHODS

(71) Applicant: General Electric Company, Schenectady, NY (US)

(72) Inventors: Namita Kohli, Chicago, IL (US); Priya Padate, Chicago, IL (US)

(73) Assignee: General Electric Company, Schenectady, NY (US)

( * ) Notice: Subject to any disclaimer, the term of this patent is extended or adjusted under 35 U.S.C. 154(b) by 183 days.

(21) Appl. No.: 16/196,937

(22) Filed: Nov. 20, 2018

(65) Prior Publication Data

US 2019/0156921 A1    May 23, 2019

Related U.S. Application Data

(60) Provisional application No. 62/590,104, filed on Nov. 22, 2017.

(51) Int. Cl.
*G16H 10/20* (2018.01)
*G06N 20/00* (2019.01)
(Continued)

(52) U.S. Cl.
CPC ......... *G16H 10/20* (2018.01); *G06F 16/3329* (2019.01); *G06F 16/538* (2019.01);
(Continued)

(58) Field of Classification Search
CPC ........ G16H 10/20; G16H 15/00; G16H 50/70; G16H 30/40; G16H 30/20; G06F 16/93;
(Continued)

(56) References Cited

U.S. PATENT DOCUMENTS

2007/0061171 A1   3/2007 Ash et al.
2008/0253693 A1*  10/2008 Chu ...................... G16H 30/20
                                                    382/128
(Continued)

OTHER PUBLICATIONS

International Searching Authority, "International Search Report and Written Opinion," issued in connection with PCT patent application No. PCT/US2018/062123, dated Feb. 25, 2019, 15 pages.
(Continued)

*Primary Examiner* — Jonathan Ng

(57) ABSTRACT

Systems, methods, and apparatus provide facilitate detection, processing, and relevancy analysis of clinical data including imaging related clinical context are disclosed and described herein. An example imaging related clinical context apparatus includes a processor to: analyze a plurality of documents to identify a subset of relevant documents in the plurality of document by: applying natural language processing to identify terms in the plurality of documents, a subset of the identified terms forming tagged concepts; processing the identified terms using a machine learning model with respect to a relevancy criterion for an examination to select the subset of relevant documents; and adding an emphasis to the tagged concepts found in the subset of relevant documents. The processor is to output the subset of relevant documents including emphasized tagged concepts.

20 Claims, 18 Drawing Sheets

(51) Int. Cl.

| | | |
|---|---|---|
| *G06F 16/93* | (2019.01) | |
| *G16H 15/00* | (2018.01) | |
| *G16H 30/40* | (2018.01) | |
| *G06F 16/332* | (2019.01) | |
| *G06F 16/538* | (2019.01) | |
| *G16H 50/70* | (2018.01) | |
| *G06F 40/30* | (2020.01) | |
| *G06F 40/40* | (2020.01) | |
| *G06N 3/08* | (2006.01) | |
| *G06N 3/04* | (2006.01) | |

(52) U.S. Cl.
CPC .............. *G06F 16/93* (2019.01); *G06F 40/30* (2020.01); *G06F 40/40* (2020.01); *G06N 20/00* (2019.01); *G16H 15/00* (2018.01); *G16H 30/40* (2018.01); *G16H 50/70* (2018.01); *G06N 3/0454* (2013.01); *G06N 3/08* (2013.01)

(58) Field of Classification Search
CPC .... G06F 16/538; G06F 16/3329; G06F 40/40; G06F 40/30; G06N 3/0454; G06N 3/08; G06N 20/00
USPC ....................................................... 705/2–3
See application file for complete search history.

(56) References Cited

U.S. PATENT DOCUMENTS

| | | | | | |
|---|---|---|---|---|---|
| 2009/0037223 | A1* | 2/2009 | Green | ................... | G16H 10/60 705/2 |
| 2011/0129131 | A1* | 6/2011 | Avinash | ................. | G16H 50/20 382/128 |
| 2013/0173284 | A1 | 7/2013 | Hyde et al. | | |
| 2013/0332182 | A1* | 12/2013 | Schmidt | ................... | G16Z 99/00 705/2 |
| 2015/0025909 | A1* | 1/2015 | Hayter, II | .............. | G16H 30/20 705/3 |
| 2015/0193583 | A1* | 7/2015 | McNair | .................. | G16H 50/20 705/2 |
| 2016/0019365 | A1* | 1/2016 | Ober, Jr. | ................ | G16H 50/70 705/2 |
| 2016/0098540 | A1* | 4/2016 | Zamanakos | .......... | A61B 5/0022 705/2 |
| 2016/0147946 | A1 | 5/2016 | Von Reden | | |
| 2016/0147954 | A1* | 5/2016 | Ng Tari | ................. | G16H 40/20 705/3 |
| 2016/0147971 | A1 | 5/2016 | Kolowitz et al. | | |
| 2016/0232160 | A1* | 8/2016 | Buhrmann | ............ | G06F 16/367 |
| 2018/0068083 | A1* | 3/2018 | Cohen | ................... | G16H 50/20 |

OTHER PUBLICATIONS

Nandhakumar, "Clinically Significant Information Extraction from Radiology Reports," Dalhousie University Halifax, Nova Scotia, Jul. 2017, 93 pages.

Wang et al., "Clinical Information Extraction Applications: A literature review," Journal of Biomedical Informatics, Nov. 21, 2017, 16 pages.

Aberdeen et al., "The Learning Behind Gmail Priority Inbox", Google, Inc, 2010, 4 pages.

Patriarca-Almeida et al., "Using a Clinical Document Importance Estimator to Optimize an Agent-Based Clinical Report Retrieval System", 2013, 4 pages.

Hulten et al., "Mining Time-Changing Datastreams", University of Washington, 2001, 10 pages.

Rodrigues et al., "Learning from medical data streams: an introduction", 2011, 6 pages.

United States Patent and Trademark Office, "Non-Final Office action," issued in connection with U.S. Appl. No. 14/554,665, filed Nov. 13, 2018, 12 pages.

United States Patent and Trademark Office, "Final Office action," issued in connection with U.S. Appl. No. 14/554,665, filed Jul. 27, 2018, 11 pages.

United States Patent and Trademark Office, "Non-Final Office action," issued in connection with U.S. Appl. No. 14/554,665, filed Feb. 5, 2018, 9 pages.

United States Patent and Trademark Office, "Advisory action," issued in connection with U.S. Appl. No. 14/554,665, filed Jan. 3, 2018, 6 pages.

United States Patent and Trademark Office, "Final Office action," issued in connection with U.S. Appl. No. 14/554,665, filed Sep. 28, 2017, 22 pages.

United States Patent and Trademark Office, "Non-Final Office action," issued in connection with U.S. Appl. No. 14/554,665, filed Mar. 23, 2017, 14 pages.

\* cited by examiner

IMAGING RELATED CLINICAL CONTEXT APPARATUS AND ASSOCIATED METHODS

CROSS-REFERENCE TO RELATED APPLICATIONS

This patent arises from U.S. Provisional Patent Application Ser. No. 62/590,104, which was filed on Nov. 22, 2017. U.S. Provisional Patent Application Ser. No. 62/590,104 is hereby incorporated herein by reference in its entirety. Priority to U.S. Provisional Patent Application Ser. No. 62/590,104 is hereby claimed.

FIELD OF DISCLOSURE

The present disclosure relates to data event processing, and more particularly to systems, methods and computer program products to facilitate dynamic data event detection, processing, and relevancy analysis.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

BRIEF DESCRIPTION

Certain examples provide an imaging related clinical context apparatus including a memory to store instructions and data and at least one processor. The at least one processor is to at least: analyze a plurality of documents to identify a subset of relevant documents in the plurality of document by: applying natural language processing to identify terms in the plurality of documents, a subset of the identified terms forming tagged concepts; processing the identified terms using a machine learning model with respect to a relevancy criterion for an examination to select the subset of relevant documents; and adding an emphasis to the tagged concepts found in the subset of relevant documents. The at least one processor is to output the subset of relevant documents including emphasized tagged concepts.

Certain examples provide a computer-readable storage medium including instructions which, when executed, cause at least one processor to at least: analyze a plurality of documents to identify a subset of relevant documents in the plurality of document by: applying natural language processing to identify terms in the plurality of documents, a subset of the identified terms forming tagged concepts; processing the identified terms using a machine learning model with respect to a relevancy criterion for an examination to select the subset of relevant documents; and adding an emphasis to the tagged concepts found in the subset of relevant documents; and output the subset of relevant documents including emphasized tagged concepts.

Certain examples provide a computer-implemented method including: analyzing, by executing an instruction with a processor, a plurality of documents to identify a subset of relevant documents in the plurality of document by: applying natural language processing to identify terms in the plurality of documents, a subset of the identified terms forming tagged concepts; processing the identified terms using a machine learning model with respect to a relevancy criterion for an examination to select the subset of relevant documents; and adding an emphasis to the tagged concepts found in the subset of relevant documents. The example method also includes outputting, by executing an instruction with the processor, the subset of relevant documents including emphasized tagged concepts.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

Figure 1:
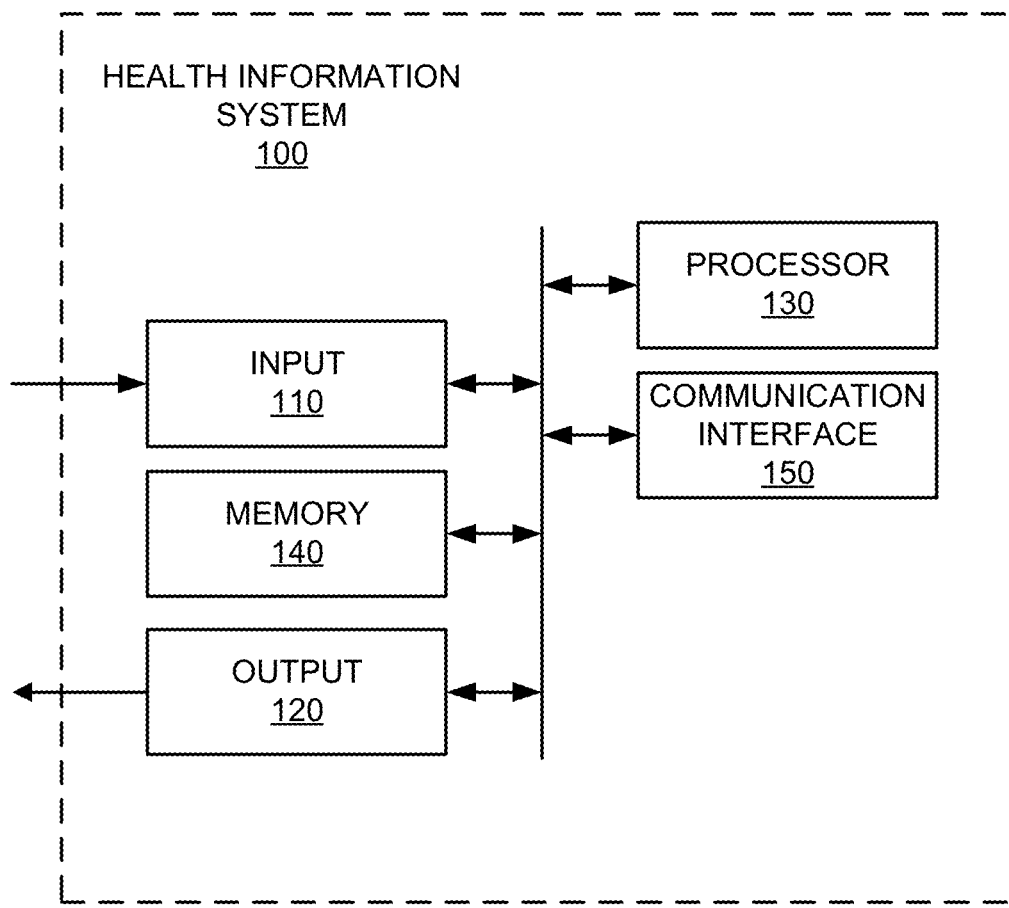
FIG. 1 shows a block diagram of an example healthcare-focused information system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

I. OVERVIEW

Research has revealed that radiologists are seeking answers to two main questions during their interpretation of imaging studies of a patient: 1. What clinical question is an ordering physician looking to answer by ordering this exam? 2. What are the patient's underlying conditions, including condition severity and impacted body region? Certain examples provide apparatus, systems, and methods to generate and capture imaging related clinical context (IRCC) to answer these questions and provide new resources, analysis, routing, and computer-aided options for diagnosis, treatment, etc., through new technology and technological innovation in the field of image processing and image- and data-driven healthcare systems.

Certain examples provide IRCC to deliver relevant patient context to radiologists when they are reviewing images. Patient context includes surgical notes, pathology reports, and clinical notes, which are delivered directly to radiologists and embedded in their existing workflow. The IRCC algorithm learns from radiologists via keywords and sentence structure how to select relevant clinical data, for example.

Certain examples enable exam, patient, and image-specific information retrieval from disparate source systems and generate a visualization of the retrieved information, individually and/or in combination, to reveal new insights to improve image processing and analysis, other health-related data processing and analysis, and technologies for patient care to improve a radiologist's ability to complete crucial tasks across the imaging continuum.

A sudden growth in EMR adoption creates an abundance of healthcare data. As healthcare providers need to maintain historic patient records, this amount of data continues to increase. This rapid accumulation of data includes case notes, imaging data, exam and procedure reports, lab values, pathology reports, and other diagnostic data. As the use of bidirectional patient portals increases, patients' uploaded data, such as white visible light images, blood pressure, blood sugar, and other home monitoring data adds to the available information. The massive volume of patient related data makes it very difficult, even impossible, to thoroughly review the data and sort out what is clinically relevant in any given patient care context such as in the reading of an exam.

In a radiological examination, a patient's clinical history and indication (CHI) are critical components of a quality interpretation, as this data provides a context in which acute symptoms and findings can be interpreted more accurately. Pertinent and accurate information relating to current symptoms and past medical history enable the radiologist to interpret imaging findings in the appropriate clinical context. The appropriate clinical context and interpretation of findings then leads to a more relevant differential diagnosis, a more useful report for the clinician, and, ideally, a better outcome for the patient.

However, studies demonstrate that relevant medical information is often lacking in the information communicated to the radiologist in exam orders. This lack of relevant data can have a potential negative impact on quality of information interpretation. Therefore, automatically presenting aggregated patient information to the radiologist in a reading workflow helps improve interpretation and adds value to a chain of care within a radiology department.

Currently, radiologists can access patient records in other systems such as an electronic medical records (EMR) system, but, accessing patient records in the EMR is often time consuming, given that the radiologist needs to access a separate system, then click through many layers of menus in search of clinically relevant data. Certain examples address the technological need in the industry by providing systems, apparatus, and methods to automatically collect and aggregate this information and then provide it to the radiologist in the context of the reading workflow.

In certain examples, the IRCC links in real time (or substantially real time given data storage, retrieval, transmission, and/or processing latency, etc.) to one or more external systems to collect and embed data, such as clinical notes, pathology reports, lab results, surgical notes, etc., in the workflow. As a result, a patient's relevant clinical content is presented in context so that clinicians can gain a more complete picture of the patient to more quickly reach a confident diagnosis.

The IRCC can be used to retrieve exam, patient, and image-specific information from disparate source systems and visualize that information to reveal new insights to help improve a user's ability to complete tasks across the imaging continuum. Rather than assuming that a radiologist's content at the start of their workflow will remain the same until a report is finalized, certain examples flexibly retrieve and display information as radiologist's needs change, e.g., from exam to exam, within an exam, etc.

The IRCC eliminates the need for the radiologist to log into another application, look up a patient identifier (ID), search for documents, and go fishing for information that might be relevant. Thus, the IRCC enables the user to save valuable time and shortens the time to diagnosis the patient. However, given the sheer amount of data often existing on a patient, especially one with a chronic condition, a challenge becomes how to present the right information to the radiologist in the context of the exam without getting lost in all the data.

In certain examples, artificial intelligence (AI) is implemented as a clinical assistant to identify key, relevant data related to an exam type and present information in a concise, quickly readable format. The AI can learn over time what information is most useful for a radiologist for each type of read. The AI can facilitate finding, filtering and ranking the relevant clinical information to aid in diagnosis and display pertinent information in a condensed format for easy readability. While the EMR provides structured and unstructured data, the IRCC enables organization, analysis, and presentation of information as structured data in the radiologists' workflow, rather than in disparate application(s). The AI in the IRCC can process the structured data to filter and prioritize. The filtering by the AI saves time, and the prioritizing by the AI adds value.

Rather than trying to provide an algorithm that provides the one "right document" the radiologist needs, certain examples provide apparatus, systems, and methods that learn clinical relevance from users. For example, terms can be highlighted in the most relevant paragraphs and feedback can be gained in the context of the reading to determine whether the data was useful or not. A deep learning algorithm can incorporate this feedback to learn over time how to best select and present relevant clinical data based upon the type of read. For example, a database of usage information can be generated by monitoring what users click on and view. From the set of usage information, patterns of usage can be determined and leveraged. Thus, certain examples drive a convergence between interpreting electronic health record data and interpreting images to provide clinical decision support integrated with image interpretation.

For example, notes and other communication authored by the physician who ordered an exam can be identified and retrieved as part of the exam review. These notes can be parsed to identify sections in which the physician provided information regarding an intent to order the exam, mentioned the same modality and/or body region, mentioned a reason for exam and/or history, etc. Determining the reason for exam can help to process the available documentation and extract relevant portions related to the reason for the exam.

Certain examples interpret patient and exam context, including a reason for exam, to provide an answer to a query regarding the patient's underlying condition and documentation that supports them. Environmental context (e.g., inpatient, outpatient, emergency department, etc.) of an exam can help with proper interpretation. Body region and/or body part can be analyzed to identify a probable affected area to focus on the diagnosis and extract/highlight relevant information as evidence to support diagnosis, for example. Disease category (e.g., trauma, vascular, infection, neoplasm, metabolic, etc.) and current phase of treatment (e.g., screening, follow-up, pre/post-surgery, etc.) at the point of exam can also be used to process available documentation to extract and/or highlight relevant information, for example.

Aspects disclosed and described herein enable information aggregation and information filtering that cannot be accomplished in a current clinical workflow. Constantly changing large datasets dispersed across multiple systems make it difficult and time consuming to not only find important information, but also link this important information together to create a coherent patient story, for example.

Certain examples provide IRCC to retrieve exam, patient, and image specific information out of disparate source systems and visualize the information to reveal new insights to help improve a user's ability to complete crucial tasks across the imaging continuum.

Additionally, clinical context changes. Thus, IRCC can be provided throughout a radiologist's workflow, not just provided at the start of their workflow with an assumption that the same content will suffice until the report is finalized. Certain examples enable flexible retrieval and display of information radiologists' needs change, from exam to exam and within an exam. The IRCC can help drive a workflow including a reason for exam, orienting the patient and/or user with respect to the exam, interpreting exam results, and reporting exam results, for example.

Certain examples provide context to orient the IRCC system with respect to a question an ordering physician is looking to answer by ordering an exam. To answer this question, the IRCC system identifies notes and other communication authored by the physician who ordered the exam. Within these notes, the IRCC system identifies sections in which the physician documents an intent to order the exam, mentions the same modality/body region, mentions a reason for the exam and history, etc.

Certain examples provide context to interpret available information to automatically determine a patient's underlying condition(s) and develop supporting documentation. Using an environmental context of the exam, a probable affected anatomical area of diagnosis, a disease category, and the patient's current phase of treatment at the point of the exam, the IRCC system can determine the patient's condition(s) and develop documentation, notification, protocol, etc., to support a healthcare practitioner in responding to that patient (e.g., diagnosing, referring, treating, etc., the patient). For example, the environmental context of the exam can include inpatient vs. outpatient vs. emergency department (ED), etc. A probable affected anatomical area of diagnosis can include a number of body regions that may provide evidence to support the diagnosis, etc. The disease category can include trauma, vascular, infection, neoplasm, metabolic, etc. The patient's current phase of treatment at the point of the exam can include screening, follow-up, pre-/post-surgery, etc.

Thus, for example, obtaining a reason for exam helps to drive organization of disparate data into a cohesive patient record for diagnosis, treatment, execution of a patient care plan, etc. Reasons for exam can be symptom-based and driven to find a cause of the symptoms, for example. For example, if a reason for exam (RFE) is a rib fracture, the IRCC system can interpret the RFE as chest pain to avoid initial assumptions until additional context is determined. Additionally, if a patient has a history of rheumatological illness, then presence of erosion is a different indication than a healthy person with presence of erosion. Providing the patient/clinical context enables more accurate diagnosis and determination of next steps in a plan of care for that particular patient.

Certain examples provide an intelligent recommendation system that automatically displays medical information determined to be relevant to end user(s) for a particular clinical scenario. The example intelligent recommendation system leverages natural language processing (NLP) to generate data from unstructured content; machine learning techniques to identify global usage patterns of data; and feedback mechanisms to train the system for personalized performance.

In certain examples, an apparatus responds to data source events through data source triggers and/or polling. Once data is received at the apparatus, the data is processed using available natural language processing tools to create document meta data. Document meta data is used to calculate similarity/dissimilarity of data and generate data summarization. Upon process completion, an output of natural language processing is coupled with additional data that summarizes data usage to create a robust feature set. Machine learning techniques are then applied to the feature set to determine data relevancy. Consumers can access relevant data through one or more Application Programming Interfaces (APIs).

Data processing within an example system is initiated through consumption of data events through a queuing system. A data event consumer retrieves data for relevancy algorithmic processing at processing time. An algorithm processor service applies natural language processing and machine learning techniques to determine similarity, dissimilarity, and relevancy as well as a summarization of the data. As end users access relevant data through the system, usage metrics are collected, processed, and stored through a usage rest service. Data retrieval is sourced to a data de-identification mechanism for anonymous presentation domain level data usage statistics. Relevant meta-data is stored in a database (e.g., a NoSQL data store, etc.) to enable flexible and robust analysis.

A relevancy algorithm combines aspects of domain specific knowledge with user specific knowledge and user information preference. A domain model filters global usage allowing only those points by users that are relevant to a clinical situation (e.g., only users specific to the current/selected workflow, etc.). Users are able to indicate data preference through a rating system (e.g., like/dislike, relevant/not-relevant, star rating, etc.).

Data preference and relevancy can be determined with respect to a radiology workflow and/or radiology desktop application interface, for example. An example radiology desktop provides an interaction framework in which a worklist is integrated with a diagnostic space and can be manipulated into and out of the diagnostic space to progress from a daily worklist to a particular diagnosis/diagnostic view for a patient (and back to the daily worklist). The radiology desktop shows the radiologist what is to be done and on what task(s) the radiologist is current working. In certain examples, the radiology desktop provides a diagnostic hub and facilitates a dynamic workflow and adaptive composition of a graphical user interface.

Other aspects, such as those discussed in the following and others as can be appreciated by one having ordinary skill in the art upon reading the enclosed description, are also possible.

II. EXAMPLE OPERATING ENVIRONMENT

Health information, also referred to as healthcare information and/or healthcare data, relates to information generated and/or used by a healthcare entity. Health information can be information associated with health of one or more patients, for example. Health information can include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure can include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

a. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. The example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of the example system 100 can be integrated in one device or distributed over two or more devices.

The example input 110 can include a keyboard, a touch-screen, a mouse, a trackball, a track pad, optical barcode recognition, voice command, etc. or combination thereof used to communicate an instruction or data to the system 100. The example input 110 can include an interface between systems, between user(s) and the system 100, etc.

The example output 120 can provide a display generated by the processor 130 for visual illustration on a monitor or the like. The display can be in the form of a network interface or graphic user interface (GUI) to exchange data, instructions, or illustrations on a computing device via the communication interface 150, for example. The example output 120 can include a monitor (e.g., liquid crystal display (LCD), plasma display, cathode ray tube (CRT), etc.), light emitting diodes (LEDs), a touch-screen, a printer, a speaker, or other conventional display device or combination thereof.

The example processor 130 includes hardware and/or software configuring the hardware to execute one or more tasks and/or implement a particular system configuration. The example processor 130 processes data received at the input 110 and generates a result that can be provided to one or more of the output 120, memory 140, and communication interface 150. For example, the example processor 130 can take user annotation provided via the input 110 with respect to an image displayed via the output 120 and can generate a report associated with the image based on the annotation. As another example, the processor 130 can process updated patient information obtained via the input 110 to provide an updated patient record to an EMR via the communication interface 150.

The example memory 140 can include a relational database, an object-oriented database, a data dictionary, a clinical data repository, a data warehouse, a data mart, a vendor neutral archive, an enterprise archive, etc. The example memory 140 stores images, patient data, best practices, clinical knowledge, analytics, reports, etc. The example memory 140 can store data and/or instructions for access by the processor 130. In certain examples, the memory 140 can be accessible by an external system via the communication interface 150.

In certain examples, the memory 140 stores and controls access to encrypted information, such as patient records, encrypted update-transactions for patient medical records, including usage history, etc. In an example, medical records can be stored without using logic structures specific to medical records. In such a manner the memory 140 is not searchable. For example, a patient's data can be encrypted with a unique patient-owned key at the source of the data. The data is then uploaded to the memory 140. The memory 140 does not process or store unencrypted data thus minimizing privacy concerns. The patient's data can be downloaded and decrypted locally with the encryption key.

For example, the memory 140 can be structured according to provider, patient, patient/provider association, and document. Provider information can include, for example, an identifier, a name, and address, a public key, and one or more security categories. Patient information can include, for example, an identifier, a password hash, and an encrypted email address. Patient/provider association information can include a provider identifier, a patient identifier, an encrypted key, and one or more override security categories. Document information can include an identifier, a patient identifier, a clinic identifier, a security category, and encrypted data, for example.

The example communication interface 150 facilitates transmission of electronic data within and/or among one or more systems. Communication via the communication interface 150 can be implemented using one or more protocols. In some examples, communication via the communication interface 150 occurs according to one or more standards (e.g., Digital Imaging and Communications in Medicine (DICOM), Health Level Seven (HL7), ANSI X12N, etc.). The example communication interface 150 can be a wired interface (e.g., a data bus, a Universal Serial Bus (USB) connection, etc.) and/or a wireless interface (e.g., radio frequency, infrared, near field communication (NFC), etc.). For example, the communication interface 150 can communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

b. Example Healthcare Infrastructure

Figure 2:
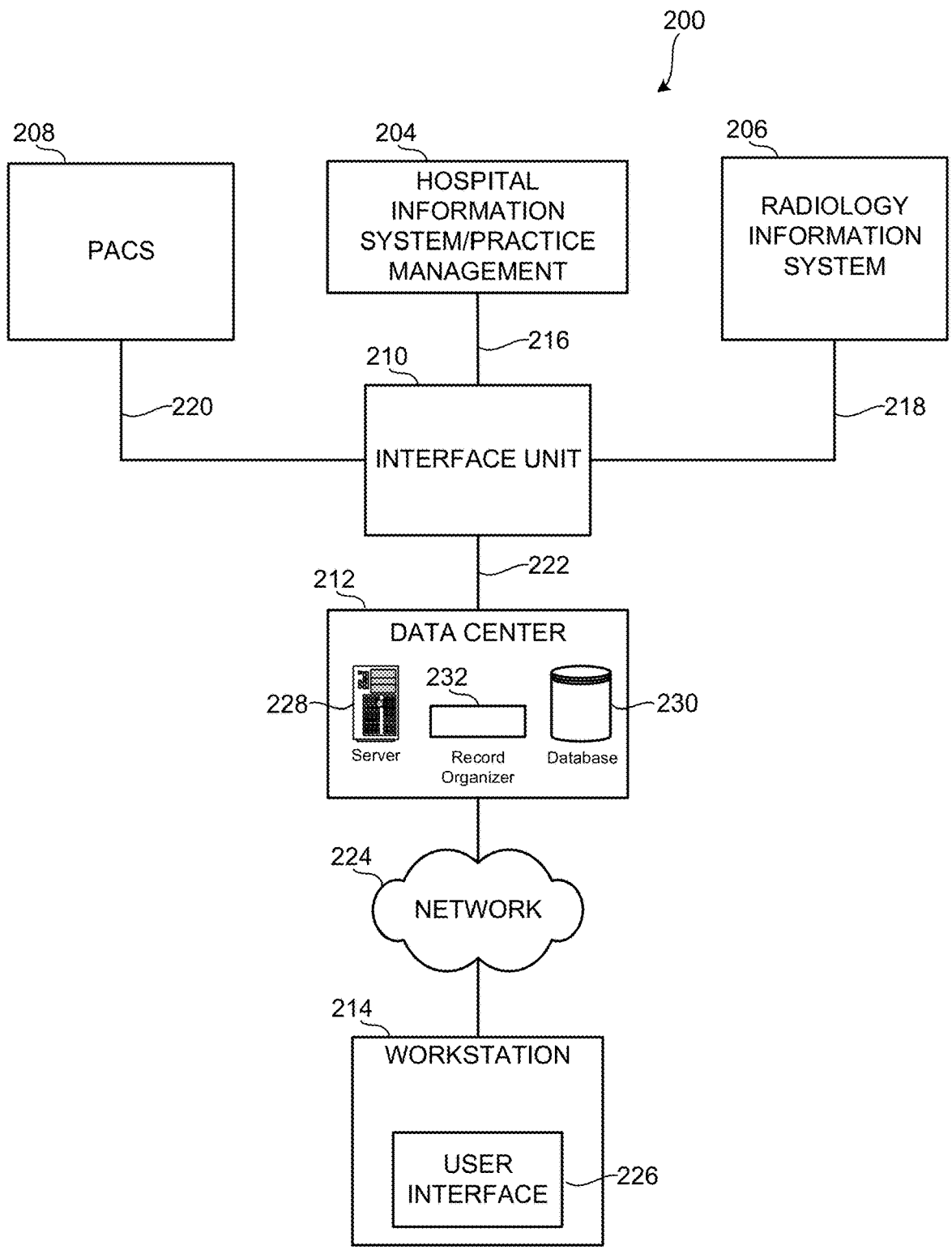
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. The example healthcare system 200 includes a HIS 204, a RIS 206, a PACS 208, an interface unit 210, a data center 212, and a workstation 214. In the illustrated example, the HIS 204, the RIS 206, and the PACS 208 are housed in a healthcare facility and locally archived. However, in other implementations, the HIS 204, the MS 206, and/or the PACS 208 can be housed one or more other suitable locations. In certain implementations, one or more of the PACS 208, MS 206, HIS 204, etc., can be implemented remotely via a thin client and/or downloadable software solution. Furthermore, one or more components of the healthcare system 200 can be combined and/or implemented together. For example, the MS 206 and/or the PACS 208 can be integrated with the HIS 204; the PACS 208 can be integrated with the MS 206; and/or the three example information systems 204, 206, and/or 208 can be integrated together. In other example implementations, the healthcare system 200 includes a subset of the illustrated information systems 204, 206, and/or 208. For example, the healthcare system 200 can include only one or two of the HIS 204, the RIS 206, and/or the PACS 208. Information (e.g., scheduling, test results, exam image data, observations, diagnosis, etc.) can be entered into the HIS 204, the RIS 206, and/or the PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). The MS 206 stores information such as, for example, radiology reports, radiology exam image data, messages, warnings, alerts, patient scheduling information, patient demographic data, patient tracking information, and/or physician and patient status monitors. Additionally, the MS 206 enables exam order entry (e.g., ordering an x-ray of a patient) and image and film tracking (e.g., tracking identities of one or more people that have checked out a film). In some examples, information in the MS 206 is formatted according to the HL-7 (Health Level Seven) clinical communication protocol. In certain examples, a medical exam distributor is located in the MS 206 to facilitate distribution of radiology exams to a radiologist workload for review and management of the exam distribution by, for example, an administrator.

The PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine (DICOM) format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

The interface unit 210 includes a hospital information system interface connection 216, a radiology information system interface connection 218, a PACS interface connection 220, and a data center interface connection 222. The interface unit 210 facilitates communication among the HIS 204, the RIS 206, the PACS 208, and/or the data center 212. The interface connections 216, 218, 220, and 222 can be implemented by, for example, a Wide Area Network (WAN) such as a private network or the Internet. Accordingly, the interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

The interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 214 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 214 receives commands and/or other input from a user via, for example, a keyboard, mouse, track ball, microphone, etc. The workstation 214 is capable of implementing a user interface 226 to enable a healthcare practitioner and/or administrator to interact with the healthcare system 200. For example, in response to a request from a physician, the user interface 226 presents a patient medical history. In other examples, a radiologist is able to retrieve and manage a workload of exams distributed for review to the radiologist via the user interface 226. In further examples, an administrator reviews radiologist workloads, exam allocation, and/or operational statistics associated with the distribution of exams via the user interface 226. In some examples, the administrator adjusts one or more settings or outcomes via the user interface 226.

The example data center 212 of FIG. 2 is an archive to store information such as images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider (ASP) and is located in a centralized location that can be accessed by a plurality of systems and facilities (e.g., hospitals, clinics, doctor's offices, other medical offices, and/or terminals). In some examples, the data center 212 can be spatially distant from the HIS 204, the MS 206, and/or the PACS 208 (e.g., at GENERAL ELECTRIC® headquarters).

The example data center 212 of FIG. 2 includes a server 228, a database 230, and a record organizer 232. The server 228 receives, processes, and conveys information to and from the components of the healthcare system 200. The database 230 stores the medical information described herein and provides access thereto. The example record organizer 232 of FIG. 2 manages patient medical histories, for example. The record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by the system 200 via a software-as-a-service (SaaS) implementation over a cloud or other computer network, for example. In certain examples, all or part of the system 200 can also be provided via platform as a service (PaaS), infrastructure as a service (IaaS), etc. For example, the system 200 can be implemented as a cloud-delivered Mobile Computing Integration Platform as a Service. A set of consumer-facing Web-based, mobile, and/or other applications enable users to interact with the PaaS, for example.

c. Industrial Internet Examples

The Internet of things (also referred to as the "Industrial Internet") relates to an interconnection between a device that can use an Internet connection to talk with other devices on the network. Using the connection, devices can communicate to trigger events/actions (e.g., changing temperature, turning on/off, provide a status, etc.). In certain examples, machines can be merged with "big data" to improve efficiency and operations, provide improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
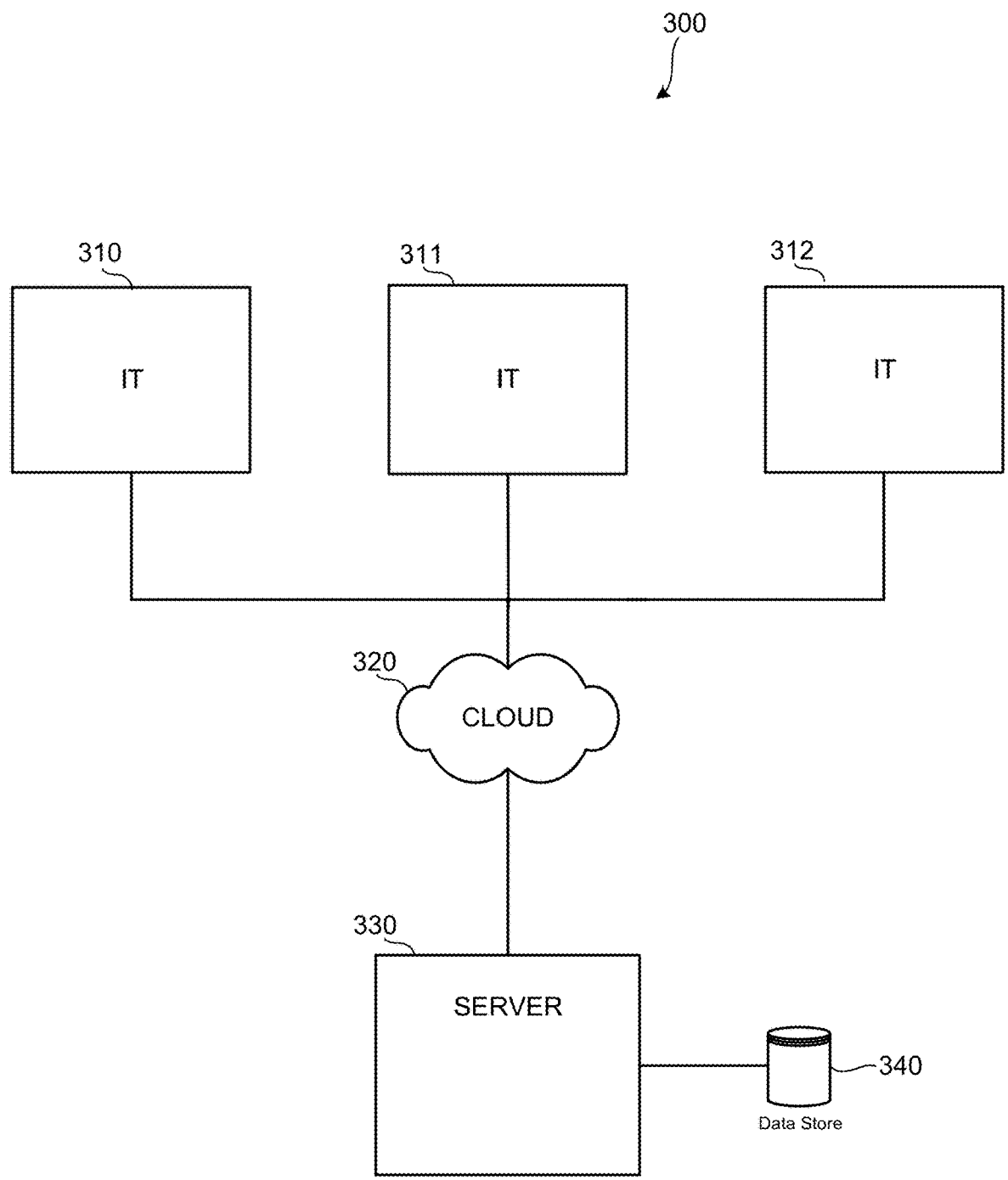
FIG. 3 shows an example industrial internet configuration including a plurality of health-focused systems.

FIG. 3 illustrates an example industrial internet configuration 300. The example configuration 300 includes a plurality of health-focused systems 310-312, such as a plurality of health information systems 100 (e.g., PACS, RIS, EMR, etc.) communicating via the industrial internet infrastructure 300. The example industrial internet 300 includes a plurality of health-related information systems 310-312 communicating via a cloud 320 with a server 330 and associated data store 340.

As shown in the example of FIG. 3, a plurality of devices (e.g., information systems, imaging modalities, etc.) 310-312 can access a cloud 320, which connects the devices 310-312 with a server 330 and associated data store 340. Information systems, for example, include communication interfaces to exchange information with server 330 and data store 340 via the cloud 320. Other devices, such as medical imaging scanners, patient monitors, etc., can be outfitted with sensors and communication interfaces to enable them to communicate with each other and with the server 330 via the cloud 320.

Thus, machines 310-312 in the system 300 become "intelligent" as a network with advanced sensors, controls, and software applications. Using such an infrastructure, advanced analytics can be provided to associated data. The analytics combines physics-based analytics, predictive algorithms, automation, and deep domain expertise. Via the cloud 320, devices 310-312 and associated people can be connected to support more intelligent design, operations, maintenance, and higher server quality and safety, for example.

Using the industrial internet infrastructure, for example, a proprietary machine data stream can be extracted from a device 310. Machine-based algorithms and data analysis are applied to the extracted data. Data visualization can be remote, centralized, etc. Data is then shared with authorized users, and any gathered and/or gleaned intelligence is fed back into the machines 310-312.

d. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

e. Example Clinical Workflows

Clinical workflows are typically defined to include one or more steps, elements, and/or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions, elements, and/or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows can include manual actions, elements, and/or steps to be taken, for example, an administrator or practitioner, electronic actions, elements, and/or steps to be taken by a system or device, and/or a combination of manual and electronic action(s), element(s), and/or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

For example, a radiology department in a hospital, clinic, or other healthcare facility facilitates a sequence of events for patient care of a plurality of patients. At registration and scheduling, a variety of information is gathered such as patient demographic, insurance information, etc. The patient can be registered for a radiology procedure, and the procedure can be scheduled on an imaging modality.

Before the patient arrives for the scheduled procedures, pre-imaging activities can be coordinated. For example, the patient can be advised on pre-procedure dietary restrictions, etc. Upon arrive, the patient is checked-in, and patient information is verified. Identification, such as a patient identification tag, etc., is issued.

Then, the patient is prepared for imaging. For example, a nurse or technologist can explain the imaging procedure, etc. For contrast media imaging, the patient is prepared with contrast media etc. The patient is guided through the imaging procedure, and image quality is verified. Using an image viewer and reporting tools, the radiologist reads the resulting image(s), performs dictation in association with the images, and approves associated reports. A billing specialist can prepare a claim for each completed procedure, and claims can be submitted to an insurer.

III. EXAMPLE MEDICAL INFORMATION ANALYSIS AND RECOMMENDATION SYSTEMS

In certain examples, a workflow manager (e.g., a radiology workflow manager) includes an Imaging Related Clinical Context (IRCC) feature to retrieve, process, organize, and display clinical documents from one or more sources (e.g., EMR, EHR, PACS, RIS, enterprise archive, vendor neutral archive, etc.) to provide clinical context to assist the diagnostic process of a radiologist. The IRCC responds to predefined events in the exam workflow to pre-emptively retrieve, analyze, process, and organize relevant patient document data from healthcare system(s), caching the response data so that it can be displayed in real-time when the exam is opened in Workflow Manager by a radiologist and/or other user. The radiologist is able to orient themselves to the historical clinical information regarding the patient which aids them in making a more informed diagnosis, rather than completely relying on the imaging timeline of the patient.

IRCC provides radiologists with quick and in-context access to clinical data, processed and organized according to relevance to help improve quality of diagnostic reads. IRCC helps improve productivity by displaying the most relevant clinical information in context to the imaging study being read by the radiologist. Current systems, such as EMRs, EHRs, etc., do not include this technology and cannot provide such in-context information organized according to relevance in context and presented with image study and other exam information for radiology reading and review. For example, even if an EMR vendor would try to provide a similar solution, the EMR does not possess a patient and/or exam context to provide a similar advantage/experience to radiologist.

Certain examples leverage artificial intelligence, natural language processing, and integration with the radiology workflow to provide many technical advantages to radiologists. For example, the IRCC provides an improved understanding of the clinical history of the patient's imaging study in context. Additionally, for example, the IRCC provides quicker and better access to clinical data in conjunction with a patient's image/exam. Further, for example, the IRCC facilitates improved productivity for diagnostic reads.

Certain examples provide an intelligent recommendation system or apparatus that automatically display medical information that is relevant to the end users for the given clinical scenario. Systems/apparatus leverage natural language processing (NLP) to generate data from unstructured content. Systems/apparatus also use machine learning techniques to identify global usage patterns of data. Systems/apparatus include feedback mechanisms to train the system for personalized performance.

Figure 4:
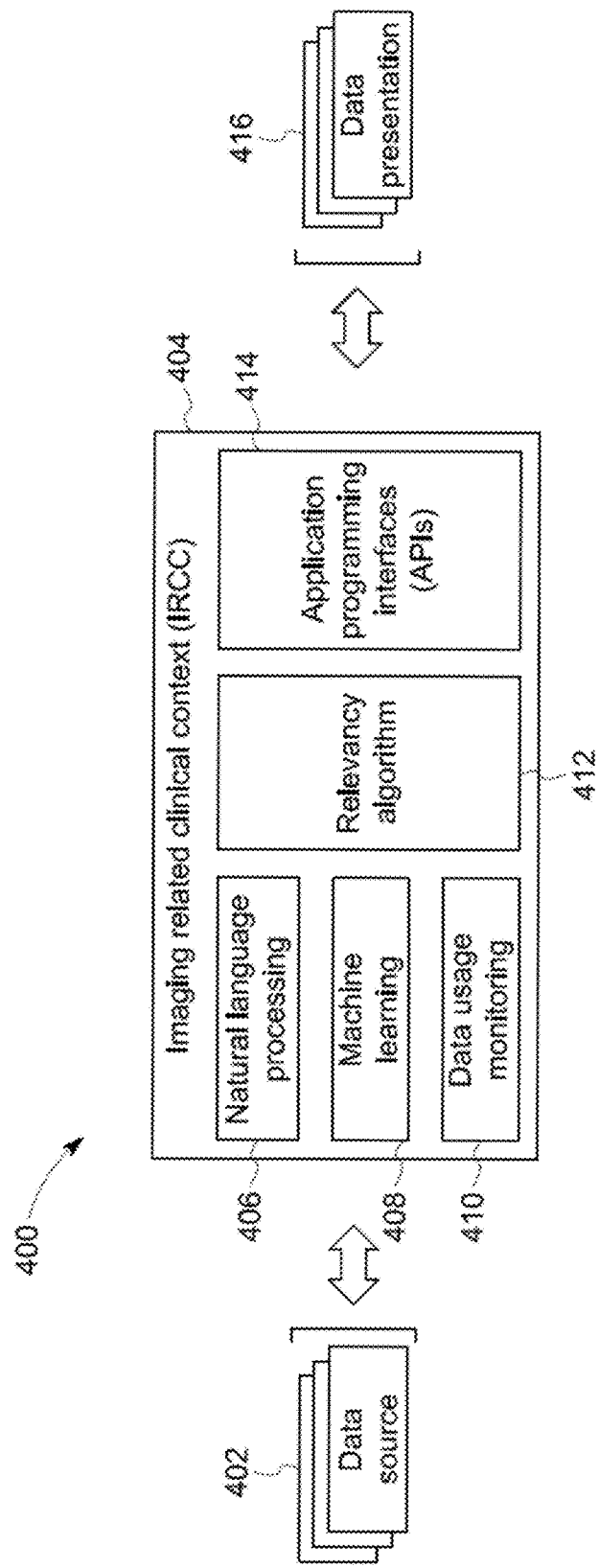
FIG. 4 illustrates an example medical information analysis and recommendation system.

FIG. 4 illustrates an example medical information analysis and recommendation system 400. The example system or apparatus 400 can be implemented in one or more systems/devices (e.g., computing devices including one or more processors) such as the systems/devices 204-208, 212, 214, 310-312, 330, etc., disclosed above. The example apparatus 400 responds to data source events through data source triggers or polling. Once data is received, the received data is processed using available natural language processing tools to create document meta data. Document meta data is used to calculate similarity/dissimilarity, and data summarization. Upon process completion, 1) an output of the natural language processing is coupled with 2) additional data that summarizes data usage to create 3) a robust feature set. Machine learning techniques are then applied to the feature set to determine data relevancy. Consumers of access relevant data through one or more Application Programming Interfaces (APIs), for example.

As shown in the example of FIG. 4, the system or apparatus 400 includes one or more data source(s) 402 communicating with an imaging related clinical context (IRCC) processor 404 to provide a data presentation 416. In certain examples, data source(s) 402 themselves may be separate from the system 400 but communicate (e.g., via the communication interface 150, and/or other wired and/or wireless connection, etc.) with the IRCC processor 404. Data source events (e.g., new documents, updated documents, lab results, exams for review, and/or other medical information, etc.) are pushed or pulled from the data source 402 to the IRCC processor 404 to trigger processing of the data from the data source. Once data is received from the data source 402 at the IRCC processor 404, the IRCC processor 404 processes the data to enrich the data and provide an indication of relevancy of the data to one or more clinical scenarios. For example, the IRCC processor 404 processes incoming data to determine whether the data is relevant to an exam for a patient being reviewed by a radiologist. Thus, the IRCC processor 404 serves as an intermediary between data sourced(s) 402 and output 416 to process an otherwise overwhelming streaming of documents and data and transform that stream into a manageable set of relevant results displayable, reviewable, and further processable to improve outcomes and safety, for example.

The IRCC processor 404 includes a natural language processor 406, a machine learning processor 408, and a data usage monitor 410. The processors 406, 408, 410 operate on the data from the data source 402 at the control of a relevancy algorithm 412 to process and provide input for the relevancy algorithm to analyze and determine relevance of the incoming data to a particular clinical scenario (or plurality of clinical scenarios/circumstances, etc.). Results of the relevancy algorithm's analysis of the data and its associated feature set are externalized as a presentation of data 416 via one or more application programming interfaces (APIs) 414.

For example, the natural language processor 406 parses and processes incoming data (e.g., document data) to create document meta data. The natural language processor 406 works with the relevancy algorithm 412 to calculate similarity and/or dissimilarity to a clinical scenario, concept, and/or other criterion, etc. Data is also summarized using the natural language processor 406. Once the data is processed by the natural language processor 406, an output of the natural language processing is coupled with data usage information provided by the data usage monitor's analysis of the data (e.g., whether a current user uses and/or how much, whether others use and/or how much, specific data usage, data type usage, and/or other feedback related to the data (e.g., how relevant the data is judged to be for a given clinical scenario, etc.). The combination of NLP meta data and data usage information creates a robust feature set for the incoming data from the data source 402, which can then be applied to the relevancy analysis 412. The machine learning processor 408 also applies machine learning techniques to the feature set to determine data relevancy based on the relevancy algorithm 412. The relevancy algorithm 412 outputs a resulting relevancy evaluation (e.g., a score, label, ranking, and/or other evaluation, etc.), and data presentation 416 can be generated for display, input into another program (e.g., an image viewer, reporting tool, patient library, comparison engine, etc.) via IRCC APIs 414, for example.

Figure 5:
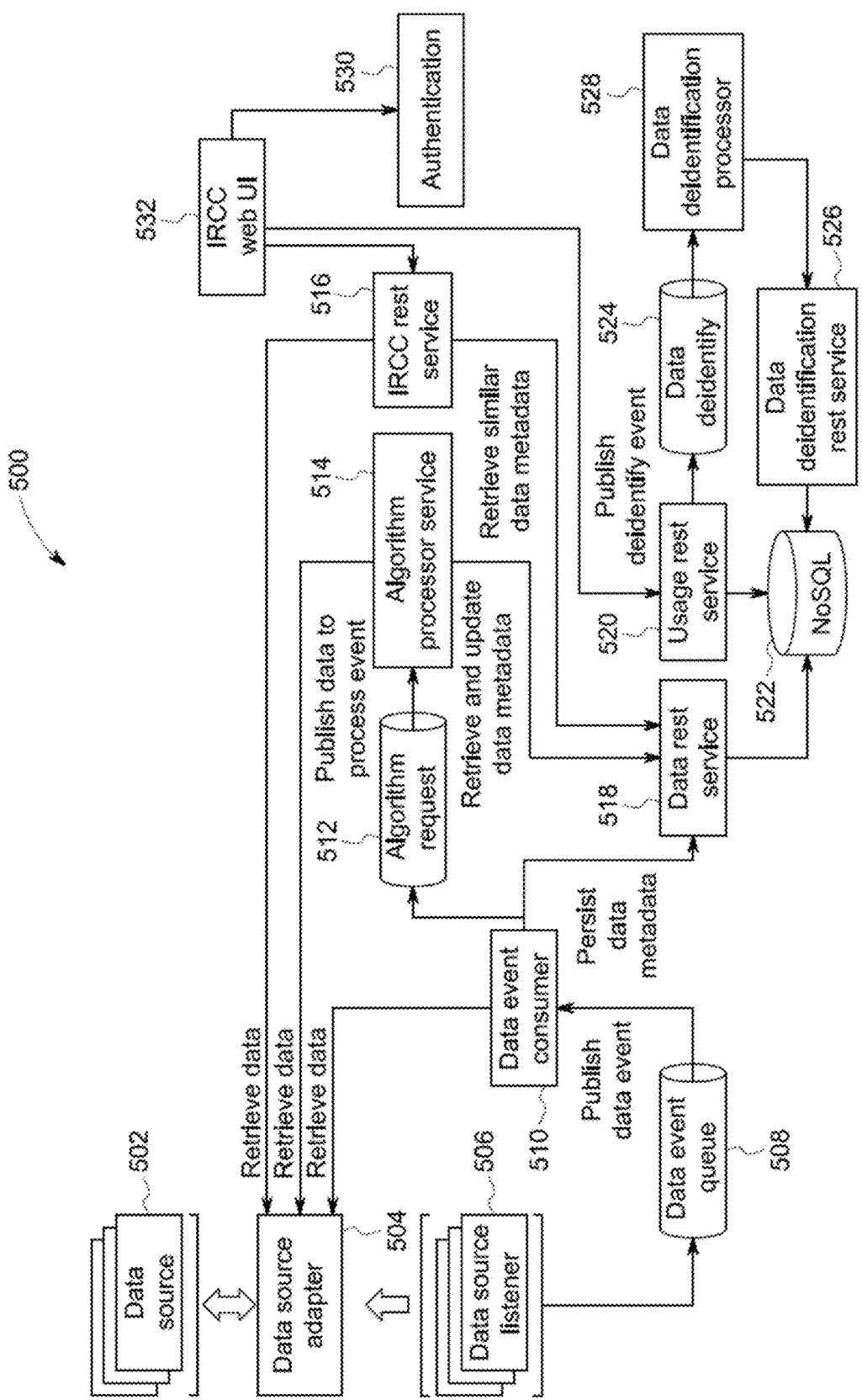
FIG. 5 illustrates an example processing system to consume data events and output a result.

In the example of FIG. 4, data processing within the system 400 is initiated or triggered by consumption of one or more data events from the data source 402 by the IRCC processor 404. The IRCC processor 404 can process events using one or more services to retrieve, format, process, and output data events (e.g., documents, document excerpts, data messages, etc.) and/or associated analysis. FIG. 5 shows an example implementation 500 of the system 400 using adapters and services.

The example system 500 includes a data source 502 (e.g., same as or similar to data source 402) in communication with a data source adapter 504. The data source adapter 504 receives input from a data source listener 506 which feeds a data event queue 508 and a data event consumer 510. The data source listener 506, data event queue 508, and/or data event consumer 510 can form or be viewed as a data event processor, for example.

The example system 500 further includes an algorithm request 512, an algorithm processor service 514, an IRCC rest service 516, a data rest service 518, a usage rest service 520, a data store 522 (e.g., NoSQL database, etc.), a data deidentifier 524, a data deidentification rest service 526, a data deidentification processor 528, an authenticator 530, and a graphical user interface 532 (e.g., an IRCC web user interface), for example. The algorithm request 512, algorithm processor service 514, IRCC service 516, data service 518, and/or usage rest service 520 can form or be viewed as a data relevancy processor, for example.

As illustrated in the example of FIG. 5, the data event consumer 510 retrieves data for relevancy algorithmic processing at processing time. The data event consumer 510 retrieves the data from the data source 520 via the data source adapter 504 which is configured to communicate with and understand one or more data source 502 to which it is connected. The data source listener 506 monitors incoming data received by the data source adapter 504 from the data source 502 and feeds the data even queue 508 when received data represents a data event (e.g., a received document, clinical data excerpt, action/result for clinical data, etc.). The data event consumer 510 consumes data events temporarily stored in the data event queue 508 and provides them based on an algorithm request 512 (e.g., data events are needed for relevancy processing). Data events are also provided by the consumer 510 to the data rest service 518 to persist data and metadata via a representational state transfer (REST) service.

The algorithm processor service 514 receives data events via the algorithm requester 512 and applies natural language processing and machine learning techniques to determine similarity, dissimilarity, and/or relevancy of the data to one or more defined criterion (e.g., a patient context, a user context, a clinical scenario, an exam, an exam type, etc.) as well as provide a summarization of the data. The algorithm processor service 514 retrieves and updates data and meta data via the algorithm requester 512.

As end users access relevant data through the system 500, usage metrics for the data are collected, processed, and stored through the usage rest service 520. Thus, as the relevancy algorithm determines that certain data is relevant to a given clinical scenario and end users 1) access and use the data, 2) do not access the data, and/or 3) access but do not use the data, the usage rest service 520 gathers and analyzes usage metrics for that data. The data 518 and its associated usage 520 can be stored in the data store 522, for example.

Data can be retrieved after being de-identified or anonymized by the data de-identification processor 528 in conjunction with the data deidentifier 524 and the data deidentification service 526. Thus, data and/or associated usage metrics can be de-identified such that an end user can benefit from relevancy without knowing the particular patient and/or user who provided the data and/or usage metric. In certain examples, based on authentication 530 of the end user, that end user may be authorized to access certain data without the data being de-identified. For example, the user may be authenticated to access his or her own data and/or usage metrics, data regarding patients under his or her care, etc. Otherwise, data deidentification occurs for anonymous presentation of domain level data usage statistics, for example. Relevant meta-data is stored in the data store 522 (e.g., a NoSQL data store) to enable flexible and robust analysis, for example.

The user interface 532 provides access to data and associated relevancy information to one or more end users, such as human users (e.g., clinicians, patients, etc.), healthcare applications (e.g., a radiology reading interface and/or other radiology desktop reporting application, etc.). A user can be authenticated 530 and provided with data, relevancy, usage, and/or other information on a push, pull, and/or other basis (e.g., push certain data based on subscription, pull other data based on user request, etc.). The services 516, 520, 526 help facilitate connection to and interaction with one or more users (e.g., human, application, system, etc.) via the interface 532, for example.

As shown in the example of FIG. 5, the IRCC service 516 can also help the data source adapter 506 communicate with the data source 502, data store 522 (via the data rest service 518), etc. The IRCC rest service 516 can retrieve similar data and/or metadata for provision via the interface 532, for example.

In certain examples, data, usage, and/or relevancy can continue to update and/or otherwise evolve through passage of time, changing circumstances, additional clinical scenarios, etc. In certain examples, the user interface 352 may indicate when updated information becomes available.

Figure 6:
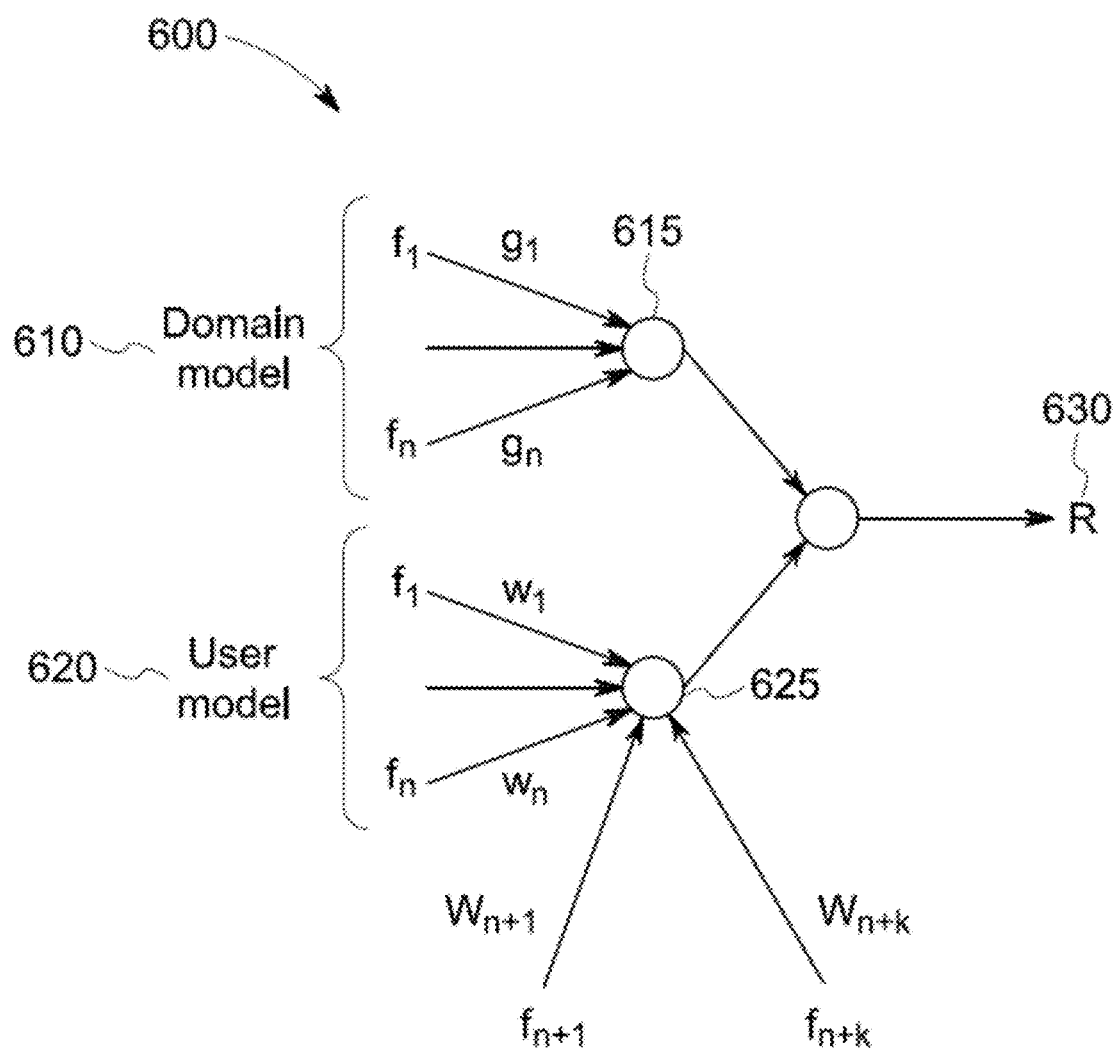
FIG. 6 illustrates an example relevancy algorithm.

FIG. 6 illustrates an example data relevancy algorithm 600. The example algorithm 600 can be employed by the relevancy algorithm 412, algorithm processor service 514, and/or other relevancy calculator, for example. The example relevancy algorithm of FIG. 6 combines aspects of domain-specific knowledge with user-specific knowledge and user information preference to determine relevancy of certain provided data to certain criterion (e.g., clinical scenario, clinician, patient, exam, condition, etc.). The example relevancy algorithm 600 includes a domain model 610 and a user model 620. The domain model 610 represents a particular clinical and/or other healthcare domain including abstractions of data and behavior occurring in that domain. Thus, the domain model 610 can model the environment in which the system 400 is being used by a radiologist and/or other healthcare practitioner, for example. For example, the domain model 610 can define entities in the domain and relationships between those entities, such as hospital, department, patient, staff, etc. The domain model 610 can include clinical history, social history, imaging history, protocol, family history, reason for exam information, surgical history, etc. The user model 620 can define or conceptualize a user (e.g., a clinician such as a radiologist, etc.) to adapt the system 400 to suit the particular user, for example.

As shown in the example of FIG. 6, the domain model 610 is organized according to data (e.g., global data, regional data, local data, etc.) regarding usage in the domain (e.g., global usage, etc.). The user model 620 is organized according to workflows to be executed by one or more users. In the example of FIG. 6, the domain model 610 filters (e.g., $f_1 \ldots f_n$) global usage (e.g., $g_1 \ldots g_n$) to identify a subset 615 of global usage for a particular domain in which the IRCC 404 is operating. The user model 620 filters users to focus on workflow(s) (e.g., $w_1 \ldots w_{n+k}$) 625 for user(s) (e.g., $f_1 \ldots f_{n+k}$) relevant to the current clinical situation. Users are able to indicate data preference through a rating system (e.g., like/dislike, relevant/not-relevant, star rating, etc.). Thus, users can provide collaborative filtering and/or recommendation to affect a result set provided as relevant. Results 615, 625 of the domain model 610 and user model 620 are combined into a result set or relevancy model R 630 indicating a relevancy of the data to the current situation (e.g., current exam for a particular user in a particular domain, etc.). Thus, documents and/or other data identified as relevant R 630 are documents/data corresponding to a selected exam for a particular patient useful to the reviewing radiologist in his/her particular department and hospital, for example.

Thus, certain examples facilitate information aggregation and information filtering beyond what previously existed within a clinical workflow. Constantly changing large datasets dispersed across multiple systems make it difficult and time consuming to not only find important information, but also link this information together to create a coherent patient story. The systems and methods of FIGS. 4-6 help to remedy these deficiencies and provide relevant data to enhance clinical review, diagnosis, and treatment, for example.

The event-based architecture of systems 400, 500 provides more efficient data processing, and natural language processing creates an easy to understand information hierarchy. The adaptable systems 400, 500 and algorithm 600 are able to respond in a variety of clinical environments. Faster display of information also leads to a more efficient workflow.

For example, the systems 400, 500 can be configured to provide a radiology encounter data display and apply heuristics to radiology data to determine relevancy to a current exam for review. Systems 400, 500 provide intelligent presentation of clinical documents in conjunction with results of the relevancy analysis. In certain examples, natural language processing is applied to clinical observational data, and resulting meta data is analyzed for an adaptive, complex relevancy determination. Adaptive and (machine) learned relevancy of clinical documents and data can then be provided. In certain examples, contextual understanding is provided for a given -ology (e.g., radiology, cardiology, oncology, pathology, etc.) to provide diagnostic decision support in context.

In certain examples, data analysis is coupled with data display to provide a hierarchical display of prior imaging and/or other clinical data. Contextual diagnostic decision support helps to facilitate improved diagnosis in radiology and/or other healthcare areas (-ologies). Knowledge engineering is applied to clinical data to generate NLP, data mining, and machine learning of radiology reports and other clinical to provide an indication of relevancy of that report/data to a given exam, imaging study, etc. Systems 400, 500 adapt and learn (e.g., machine learning) to build precision in relevancy analysis.

Figure 7:
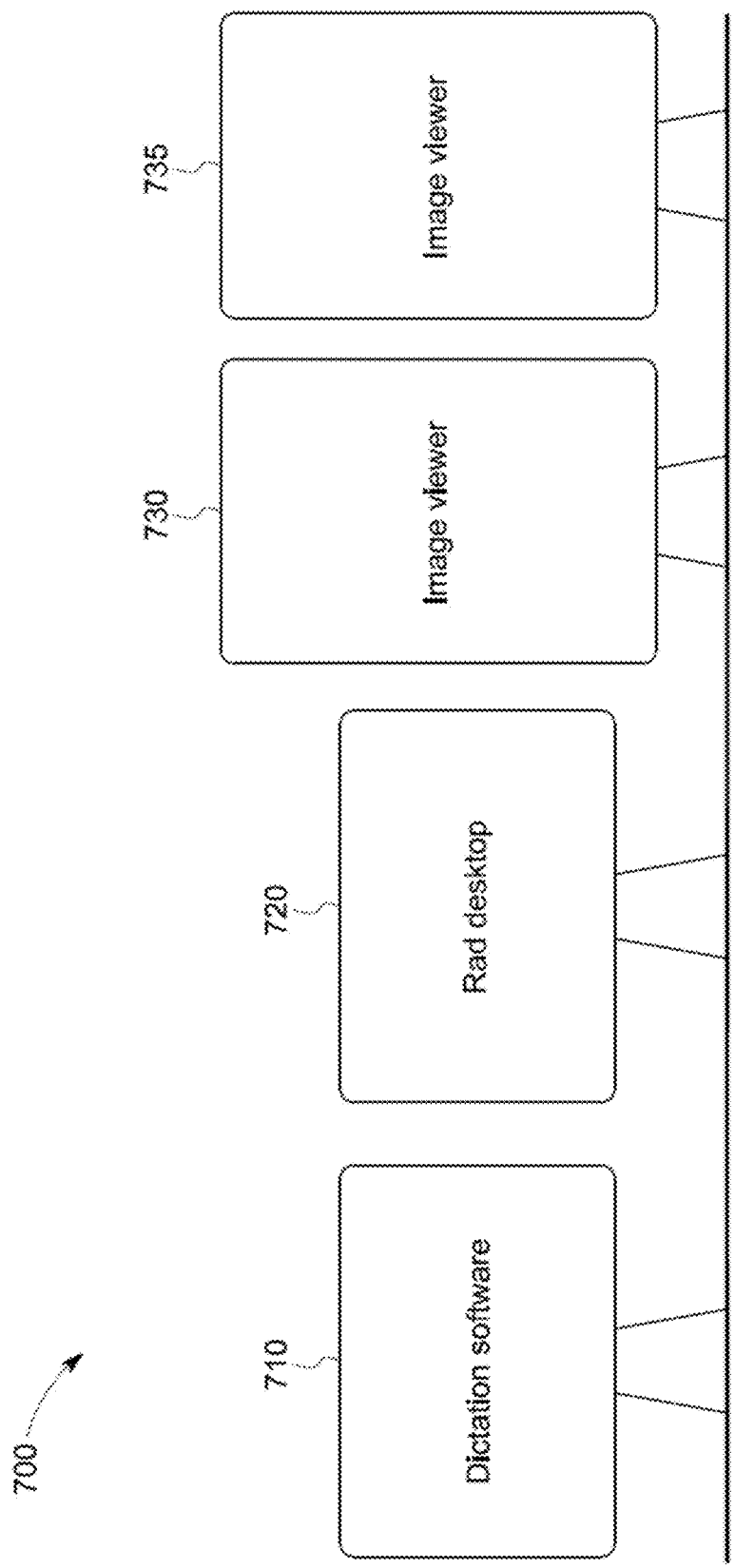
FIG. 7 shows an example image viewer and analysis system.

For example, the relevancy analysis systems and methods can be applied in the image reviewing and reporting context. In certain examples, exam imaging can be handled by a separate viewer application while dictation and report management is provided by another application. As shown in the example of FIG. 7, an image viewer is implemented on a plurality of diagnostic monitors 730, 735. A dictation application 710 either sits side-by-side with a radiology desktop or workflow manager 720, on a same monitor as the radiology desktop/workflow manager 720, or behind/in front of the radiology desktop/workflow manager 720 such that a user toggles between two windows 710, 720. In other examples, image viewing, image analysis, and/or dictation can be combined on a single workstation.

A radiologist, for example, can be presented with summary information, trending, and extracted features made available so that the radiology does not have to search through a patient's prior radiology report history. The radiologist receives decision support including relevant clinical and diagnostic information to assist in a more definitive, efficient diagnosis.

In certain examples, a current study for one or more patients X, Y, Z is prefetched from a data source 402, 502. If a current study for patient X is being processed, prior report(s) for patient X are located (e.g., from a picture archiving and communication system (PACS), enterprise archive (EA), radiology information system (RIS), electronic medical record (EMR), etc.). For example, report text and prior study metadata including a reason for exam, exam code, study, name, location, etc., are provided from a PACS as prior data for mining, extraction, and processing.

A report summary, similarity score ($s_{index}$) for each document, a summary tag for a timeline display, and select quantitative data extracts, etc., can be provided as a result of the mining, extraction, and processing of prior document data for the patient. Additionally, a value of a feature ($v_{feat}$) from a feature set provided as a result of the mining, extraction, and analysis can be determined based on one or more of modality, body part, date, referring physician, etc. Then, using $v_{feat}$ and $s_{index}$, a relevancy score can be calculated using, for example:

$$\text{Relevancy} = f(s_{index}, v_{feat}) \quad (\text{Eq. 1}).$$

Thus, relevancy is a function of an identified feature and a similarity score for identified data in comparison to a current exam, study, patient, etc.

In certain examples, a workload manager resides on a side (e.g., a left-hand side, a right-hand side, top, bottom, etc.) of a radiology desktop and can be opened or otherwise accessed to access exams. When an exam access is not desired, the workload manager can be closed or hidden with respect to the radiology desktop (e.g., with respect to a diagnostic hub on the radiology desktop). The workload manager and/or an associated diagnostic hub can leverage the information identification, retrieval, and relevancy determination systems and methods disclosed and described herein to provide information for research, comparison, supplementation, guidance, etc., in conjunction with an exam under review (e.g., via an exam preview panel from a patient library, etc.).

For example, the diagnostic hub can include a patient banner. The patient banner displays patient demographic data as well as other patient information that is persistent and true regardless of the specific exam (e.g., age, medical record number (MRN), cumulative radiation dose, etc.). The diagnostic hub also includes a primary exam preview panel. The primary exam preview panel provides a summary of the exam that the radiologist is currently responsible for reading (e.g., the exam that was selected from an active worklist). Exam description and reason for exam can be displayed to identify the exam, followed by metadata such as exam time, location, referrer, technologist, etc.

A patient library is devoted to helping a radiologist focus on relevant comparison exams, as well as any additional clinical content to aid in diagnosis. The patient library of the diagnostic hub can include subsections such as a clinical journey, comparison list, a comparison exam preview panel, etc. The clinical journey is a full patient 'timeline' of imaging exams, as well as other clinical data such as surgical and pathology reports, labs, medications, etc. The longitudinal view of the clinical journey helps the radiologist notice broader clinical patterns more quickly, as well as understand a patient's broader context that may not be immediately evident in a provided reason for the primary exam. Tools can be provided to navigate within the clinical journey. A user can adjust a time frame, filter for specific criteria, turn relevancy on or off, add or remove content categories, etc. The clinical journey also integrates with the comparison list. Modifying filter or search criteria in the clinical journey can impact the exams displayed on the comparison list.

The comparison list provides one or more available comparison exams for the current patient/primary exam. The comparison list provides a quick access point for selecting comparisons, as opposed to the more longitudinal clinical journey. Display can be limited to only show relevant exams based on the relevancy algorithm, for example. The comparison exam preview panel is similar to the primary exam preview panel, with alterations in content display to account for a radiologist's shift in priorities when looking at a comparison (e.g., selected from the comparison list, etc.). Rather than providing a reason for exam, a history and impression from the exam's report are displayed (or the whole report, if extraction is not possible or desired, etc.). The comparison previous pane also generates and/or provides a relevancy score (e.g., 0-100%) from the relevancy algorithm 600 and associated systems 400, 500 based on body part, modality, exam time, and/or other variable(s).

Thus, the diagnostic hub works with a processor, a relevancy engine, and a knowledge manager to filter and/or other process data (e.g., study data, image data, clinical data, etc.) for mining and extraction (e.g., of text), extraction (e.g., pixel data), and evaluate, via the relevancy engine, a relevance of the data to a particular exam, study, patient, etc. The knowledge manager organizes and stores relevance information for later retrieval and application in response to query and/or observer, for example.

Figure 8:
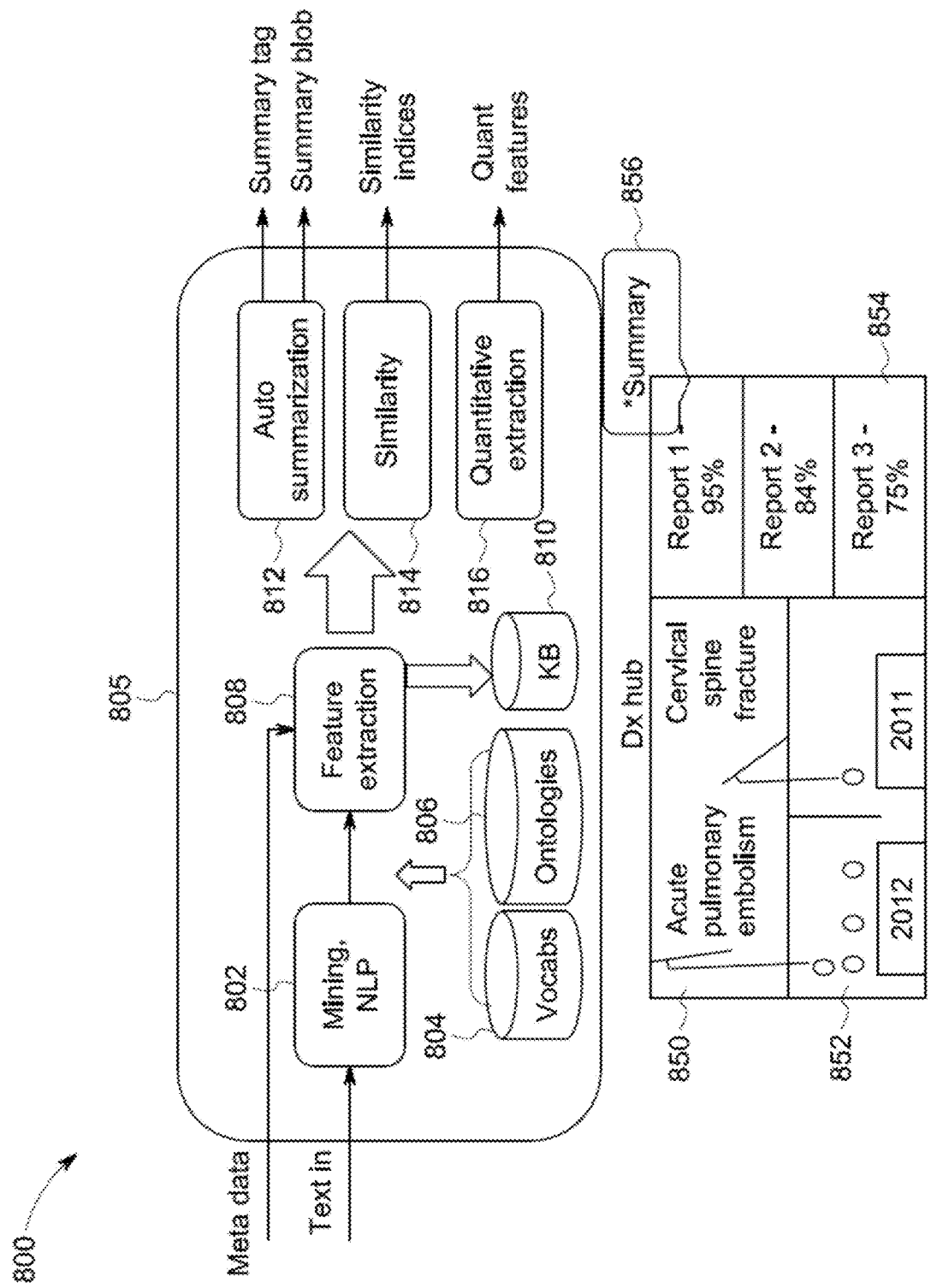
FIG. 8 illustrates an example data processing system including a processing engine and a diagnostic hub.

FIG. 8 illustrates an example data processing system 800 including a processing engine 805 and a diagnostic hub 850. The processing engine 805 processes input text documents and metadata by data mining and applying NLP techniques 802 to process the data based on one or more vocabularies 804, ontologies 806, etc. NLP output is provided for feature extraction 808. The feature extractor 808 provides feature information to a knowledge base 810 for storage, as well as for further processing.

One or more analyses are applied to the extracted features such as auto summarization 812, similarity 814, quantitative extraction 816, etc. Auto summarization 812 generates a summary tag, summary blog, etc., from one or more extracted features. Similarity 814 generates one or more similarity indices based on comparison of feature information. Quantitative extraction 816 processes extracted features and provides quantitative features. Resulting summary, similarity, and quantitative information can be stored in local and/or cloud-based document storage.

As shown in the example of FIG. 8, the diagnostic hub 850 formulates and displays reporting information based on the features and associated information provided by the processor 805. Information provided via the diagnostic hub 850 includes trending and timeline information 852, and one or more reports 854. Upon selection of (e.g., clicking on, mouse over, etc.) a report, a summary 856 of that report can be provided, for example.

Figure 9:
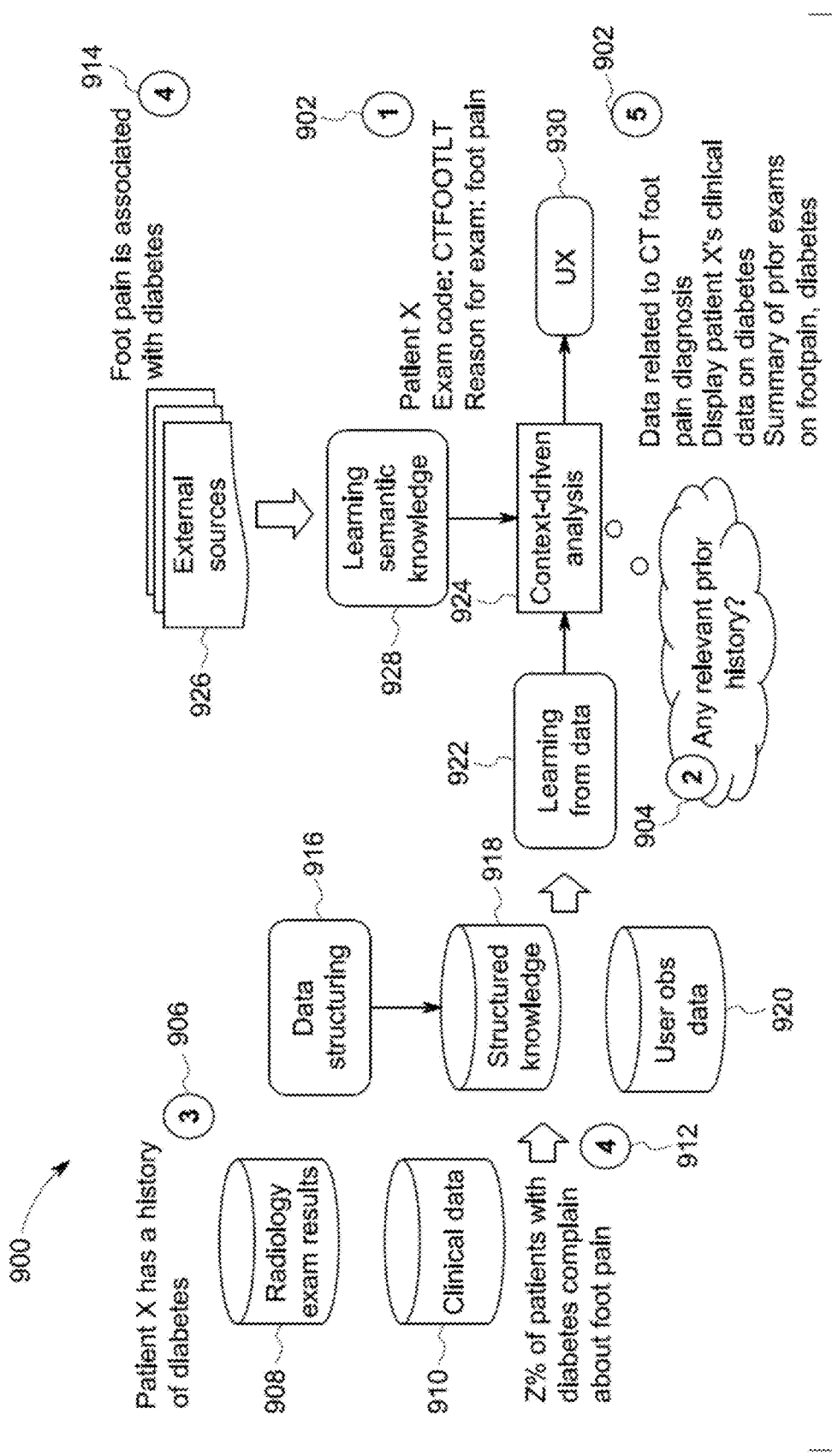
FIG. 9 shows an example context-driven analysis using an image-related clinical context relevancy algorithm.

FIG. 9 shows an example context-driven analysis 900 using an image-related clinical context relevancy algorithm. At 902, an exam is retrieved for review. For example, a patient identifier (e.g., Patient X, etc.), an exam code (e.g., CTFOOTLT, etc.), and a reason for exam (e.g., foot pain, etc.) are provided. At 904, relevant prior history for that patient, exam, reason, etc., is identified. For example, given that the reason for the exam is the patient's foot pain, prior foot images, medical history, etc., may be relevant to evaluating, diagnosing, and determining how to treat the patient's current foot pain. At 906, identified relevant history information is retrieved. For example, Patient X, who has come in for an exam including a left foot CT image due to foot pain, may have a history of diabetes. History information can come from a variety of sources such as radiology exam results 908, clinical data 910, etc. At 912 and 914, additional clinical information can be provided with the patient history information. For example, a certain percentage of patients with diabetes complain about foot pain; foot pain is associated with diabetes; etc.

Since the historical and other clinical data can come in a variety of formats, retrieved data is structured 916 to provide structured knowledge 918. User observation data 920 can also be added to supplement the structured knowledge 918. The combined data 918, 920 is then analyzed to learn from that data 922. Learning (e.g., machine learning, etc.) from the data can drive a context-driven analysis 924.

In addition to patient historical information, user observations, etc., data from external source(s) 926 can be used to drive learning semantic knowledge 928. Semantic knowledge 928 can then be used with the learning from data 922 to perform context-driven analysis 924 (e.g., including a relevancy evaluation, supplemental information, best practices, workflow, etc.).

Results of the analysis 924 are provided via a user interface 930 to a user such as a clinician, other healthcare practitioner, healthcare application (e.g., image viewer, reporting tool, archive, data storage, etc.). For example, data related to CT foot pain diagnosis; a display of Patient X's clinical data on diabetes; a summary of prior exams on foot pain, diabetes, etc.; etc., can be provided via the interface 930. Thus, via the IRCC 404, relevant patient and/or other reference data can be provided to a user in conjunction with current exam information for that patient to improve the functionality of the user interface 930 on the display 416 and improve the ability to diagnose and determine appropriate treatment for the patient.

Figure 10:
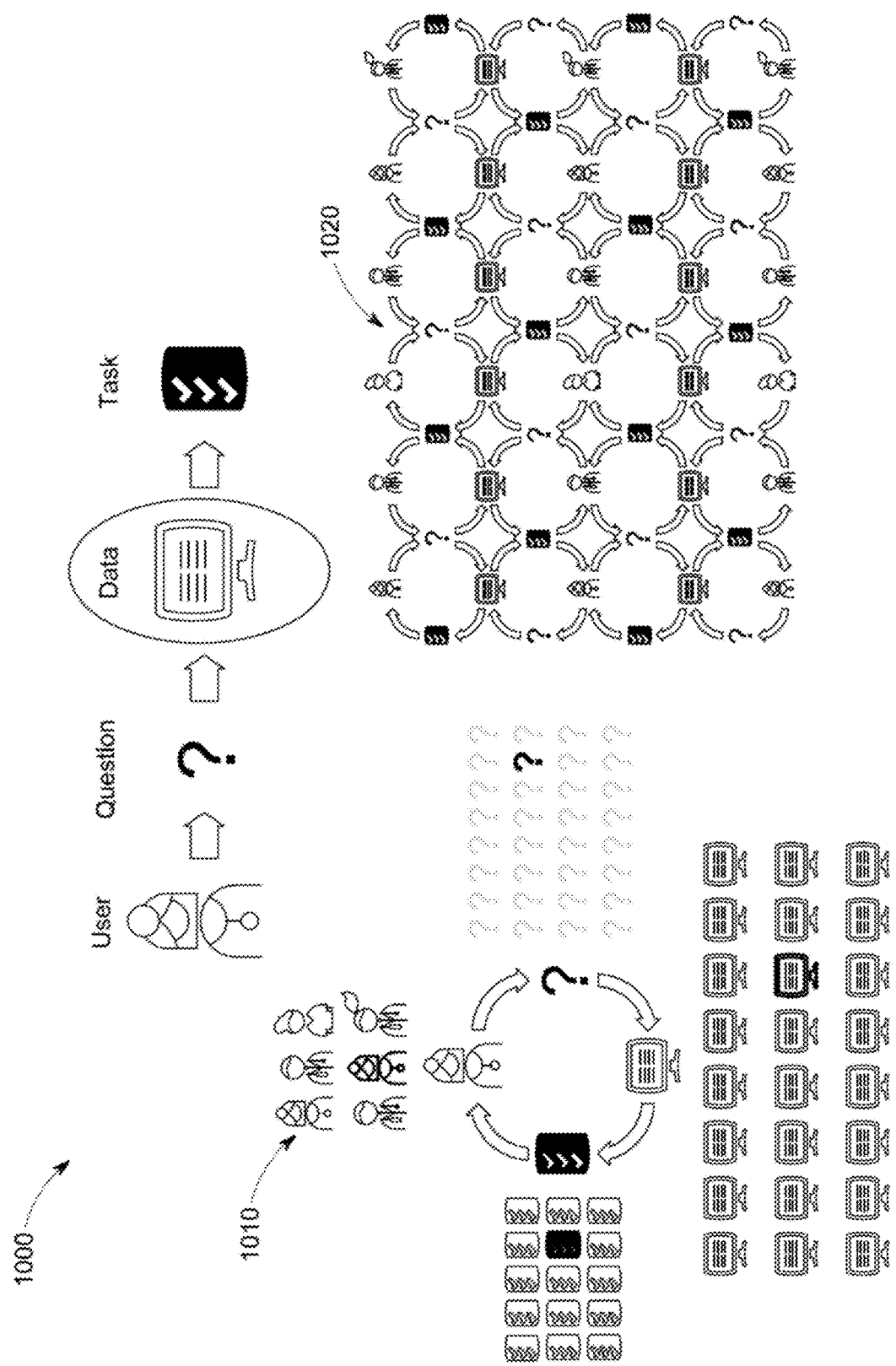
FIG. 10 shows an example imaging related clinical context-driven process.

As shown in the example of FIG. 10, an example IRCC-driven process 1000 includes determining a question of interest to a user and then organizing and applying available data to the question to generate a series of tasks to be executed to diagnose and/or provide a care plan for a patient (e.g., radiology reading, referral, treatment determination, monitoring, follow-up, etc.). As shown in the example of FIG. 10, the process 1000 can be scaled 1010 to a plurality of users with a plurality of questions leveraging to a plurality of data to drive a plurality of tasks. As illustrated at 1020, context is not static, changing over time and changing differently for different patients, users, systems, etc. The IRCC processor 404 can apply artificial intelligence to adapt to changing circumstances and data and provide changing patient and/or exam context with relevant information to a user.

Figure 11:
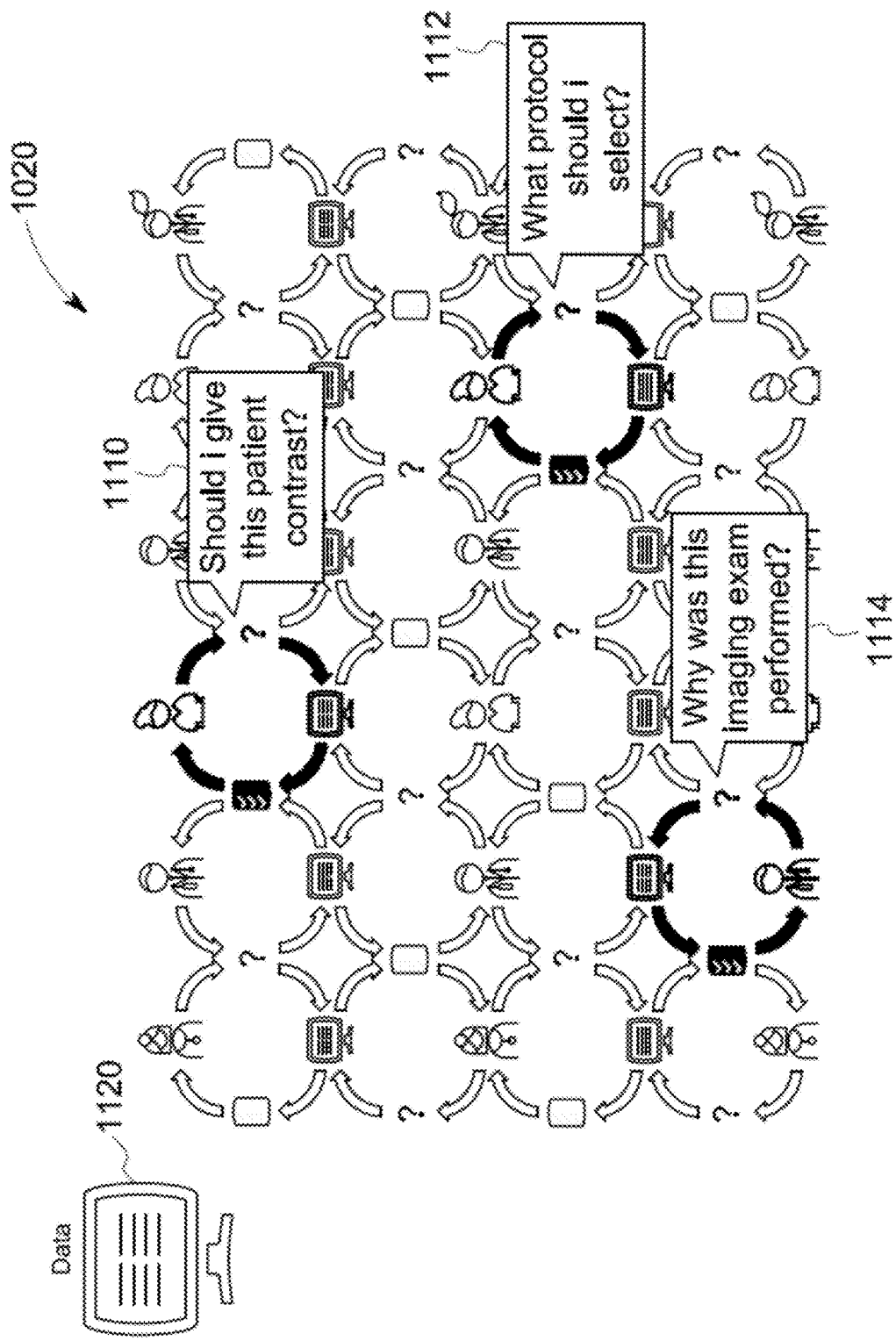
FIG. 11 illustrates further detail regarding the example changing context and identification and analysis of questions posed/reasons for exam of FIG. 10.

In certain examples, the IRCC 404 can process the changing context 1020 to further analyze questions being posed in various reviews by various users. Using AI to identify questions/RFEs posed, the IRCC 404 can provide relevant, real-time selection and analysis of documents and/or other data for automated and/or user review. FIG. 11 illustrates further detail regarding the example changing context 1020 and identification and analysis of questions posed/RFEs 1110-1114. For example, questions 1110-1114 such as whether or not to administer a contrast agent to a patient, protocol selection for a patient, reason for performing an imaging exam, etc., can be identified and analyzed to drive selection of relevant data 1120 for further processing, organization, and display. Thus, rather than providing radiologists with imaging related clinical context once at the start of their workflow and assuming that the same content will suffice until the report is finalized, clinical context is flexibly, dynamically determined and adjusted to retrieve, process, and display information as radiologists' needs and wants change from exam to exam, within an exam, etc.

In certain examples, the example workflow manager can access a clinical data store (e.g., an EMR database, EHR database, archive, etc.) and pull three types of clinical data: surgery notes, pathology notes, and clinical documentation (e.g., office visits, nursing notes, etc.) for a particular patient. The IRCC 404 processes the clinical data and displays the data in conjunction with associated patient image data at a single system with a single authentication/authorization, rather than requiring access to separate systems with separate logins and separate authentication/authorization access protocols. The IRCC 404 can pull in the data and provide the clinical data, organized according to relevance, in conjunction with image and/or other exam data for the user. When the radiologist launches a patient's imaging study from the worklist, for example, the diagnostic hub can launch the patient's imaging study and display the study in conjunction with the other clinical data (e.g., from PACS, EMR, etc.) determined to be relevant, for example.

Figure 12:
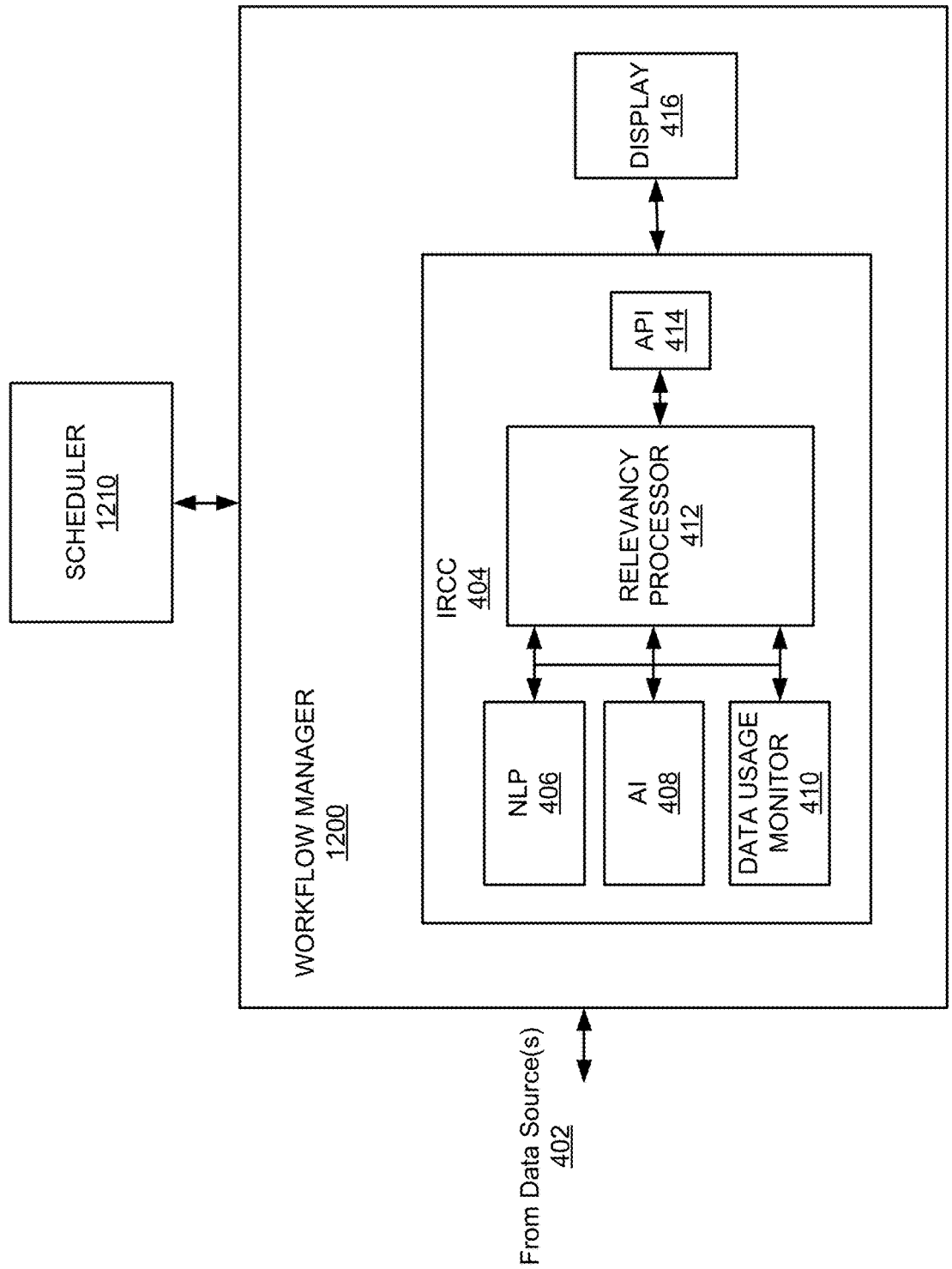
FIG. 12 illustrates an example workflow manager including an imaging related clinical context system.

The IRCC 404 ingests and digests clinical, surgical, and pathology notes and runs the notes through a natural language processor including an artificial intelligence processor, such as a convolutional neural network, other deep learning and/or machine learning network, etc. FIG. 12 illustrates an example workflow manager 1200 including the IRCC system 404. The example IRCC system 404 includes the natural language processor (NLP) 406, which leverages the artificial intelligence (AI) 408 such as a machine learning/deep learning network, etc. The NLP 406 processes incoming documents from one or more data sources 402 and generates terminology to form tagged concepts, etc., in the documents. The tagged concepts can be used by the relevancy processor 412 to prioritize the documents according to relevance. Tagged concepts and/or other terminology in the documents can be highlighted in the respective documents by the relevancy processor 412 and/or the NLP 406. The tagged, highlighted documents are ordered according to relevance, and a number of documents satisfying a threshold and/or other criterion are made available via the API 414 for presentation 416 via the workflow manager 1200.

The NLP 406 processes incoming clinical data according to one or more medical dictionaries (e.g., RadLex, NCI Thesaurus, ICD-10, CPT, LOINC, etc.). The NLP 406 ingests available documentation for a particular patient (e.g., clinical notes, surgical notes, pathology notes, etc.), processes the data, and maps text in the documents to overlapping medical terminology available through the one or more dictionaries, etc. The AI 408 can assist in making correlations, mapping, etc. The NLP 406 tabularizes matching medical terminology (e.g., disease, signs/symptoms, body regions, body parts, modality-specific information (e.g., CT abdomen pelvis chest, etc.), etc.) and tags the terminology in the documents. For example, a table and/or other data structure stored in memory can represent tagged terms or concepts to be highlighted and/or otherwise emphasized in, extracted from, etc., documents determined to be relevant, for example. Thus, the NLP 406 has a set or list of tagged terms or concepts that apply to (e.g., are found in, relate to, etc.) the patient's documents.

When a study (e.g., a CT abdomen pelvis chest imaging study, etc.) is launched via the workflow manager 1200, parameters (e.g., body region, modality, etc.) are extracted by the NLP 406 from the processed input data. The NLP 406 also processes a reason for examination from a scheduler used to schedule the exam (e.g., chest pain, etc.). Key parameters, such as reason for exam, body region (e.g., CT abdomen pelvis chest, etc.), modality (e.g., CT, MR, x-ray, ultrasound, etc.) are processed. The table of tagged concepts/terms is matched against the key parameters and input documents using a vector mapping matrix map in a convolutional neural network of the AIR 408 to generate a subset of relevant input terms from an overall set of all available terms in the documents. A threshold number of terms, such as 10, 20, 50 terms, etc., are identified as relevant for the radiologist and/or other reviewer, program processor, etc.

The NLP 406 leverages the AI 408 and the relevancy processor 412 to generate a relevance or match score for each document. For example, a paragraph-level match score can be generated for each processed clinical document. In certain examples, the highest score paragraph becomes the match score for that document. For example, the NLP 406 processes hundreds of documents and reduces the available documents to a subset (e.g., five, ten, twenty, etc.) documents of most relevance. For example, document #3 includes paragraph #3 with a 78% match, so the match score for document #3 becomes 78%. The display 416 (e.g., diagnostic hub of the workflow manager 1200, etc.) can display the document and associated match score, for example.

In certain examples, a certain threshold (e.g., top 10, top 20, top 5, etc.) of relevant documents are displayed via the workflow manager diagnostic hub when an imaging study is launched. For example, when a study is launched to evaluate a potential pneumothorax and/or other critical condition, the worklist and associated documents are automatically prioritized based on the NLP and ML analysis before being displayed to the user. The radiologist can select and view each document. In certain examples, in addition to a relevancy or match score, identified terminology, concepts, etc., tagged by the NLP 406 can be highlighted in the document. In certain examples, different colors, highlighting, bold, italics, underlining, boxes, raised or elevated text, and/or other visual and/or audible distinction can indicate different concepts, different degrees of relevance, etc., in the document and/or across multiple documents.

Thus, certain examples improve document processing and correlation technologies as well as improve user productivity. The behavior of the user interface, the make-up of the user interface, and the behavior of the processor(s) in the underlying system is altered and improved by providing technology to automatically process, analyze, and modify a subset of relevant documents for user interaction. For example, suppose a sick oncology patient comes for treatment over a period of 8-10 years. Check-ups and clinical visits for 8-10 years generates a large amount of records and documentation. However, the IRCC 404 provides the radiologist with only the top ten relevant documents including highlighted terms to enable the radiologist and/or another data processor (e.g., computer-aided diagnosis program, etc.) to skim the documents and understand the historical background and context for the patient quickly and efficiently before turning to the present imaging study, for example. Thus, key information regarding patient history, disease progression, etc., can be surfaced from a large mass of data to focus review, subsequent processing, etc.

In certain examples, the AI 408 performs vector math to determine relevancy and matching score and generate a subset of relevant documents for display. In certain examples, a worklist of exams/studies can be displayed for interaction (e.g., selection, etc.) by a user. Double-clicking on a worklist entry, for example, allows the user to see a relevant document summary and study images together, for example. Document(s) and image(s) can be selected to pull up copies of the source document, image, etc., via the viewer 416.

In certain examples, a scheduler 1210 runs daily (e.g., every night at midnight) and knows a schedule of studies for tomorrow. The scheduler 1210 understands patient IDs and can prefetch clinical data from one or more connected systems (e.g., EMR, PACS, RIS, archive, etc.). The AI 408 processes the prefetched data so that concepts are identified and tagged and documents are prepared according to schedule in advance of the user (e.g., the radiologist, etc.) launching the study. However, when the patient arrives (e.g., between midnight and 11 am the next day when patient arrives and images arrive in the system, etc.), a gap analysis is executed to identify, retrieve, and process any additional information entered after the prefetch operation (e.g., a pathology report for the patient came in between last night and the patient's appointment, etc.) to make sure the IRCC 404 is not losing out on any available data. The AI 408 processes the additional data, and concept highlighting and match score can be updated, for example.

IV. EXAMPLE INTERACTION FRAMEWORK METHODS

Figure 13:
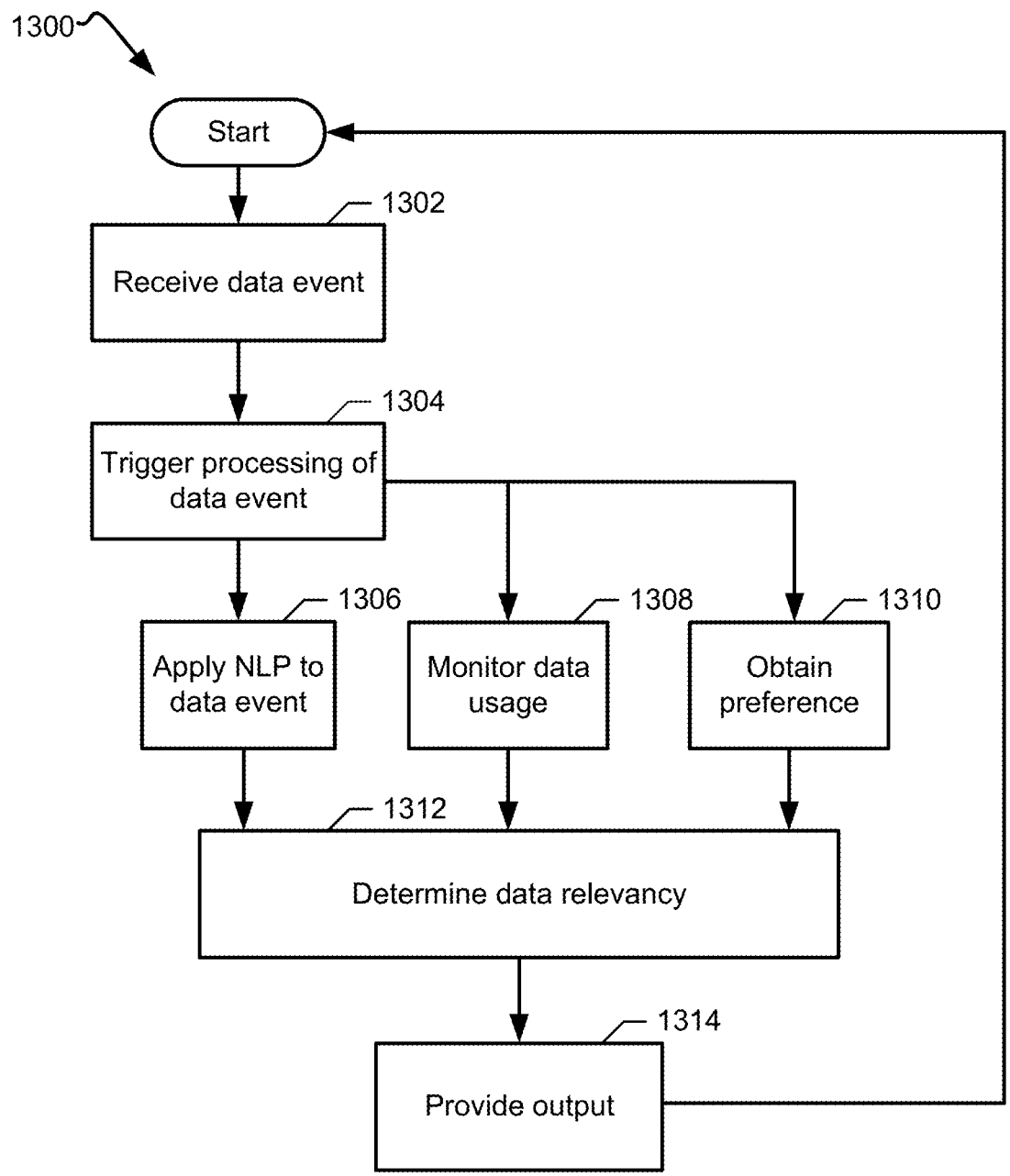
FIG. 13 illustrates a flow diagram for an example method to evaluate medical information to provide relevancy and context for a given clinical scenario.
Figure 14:
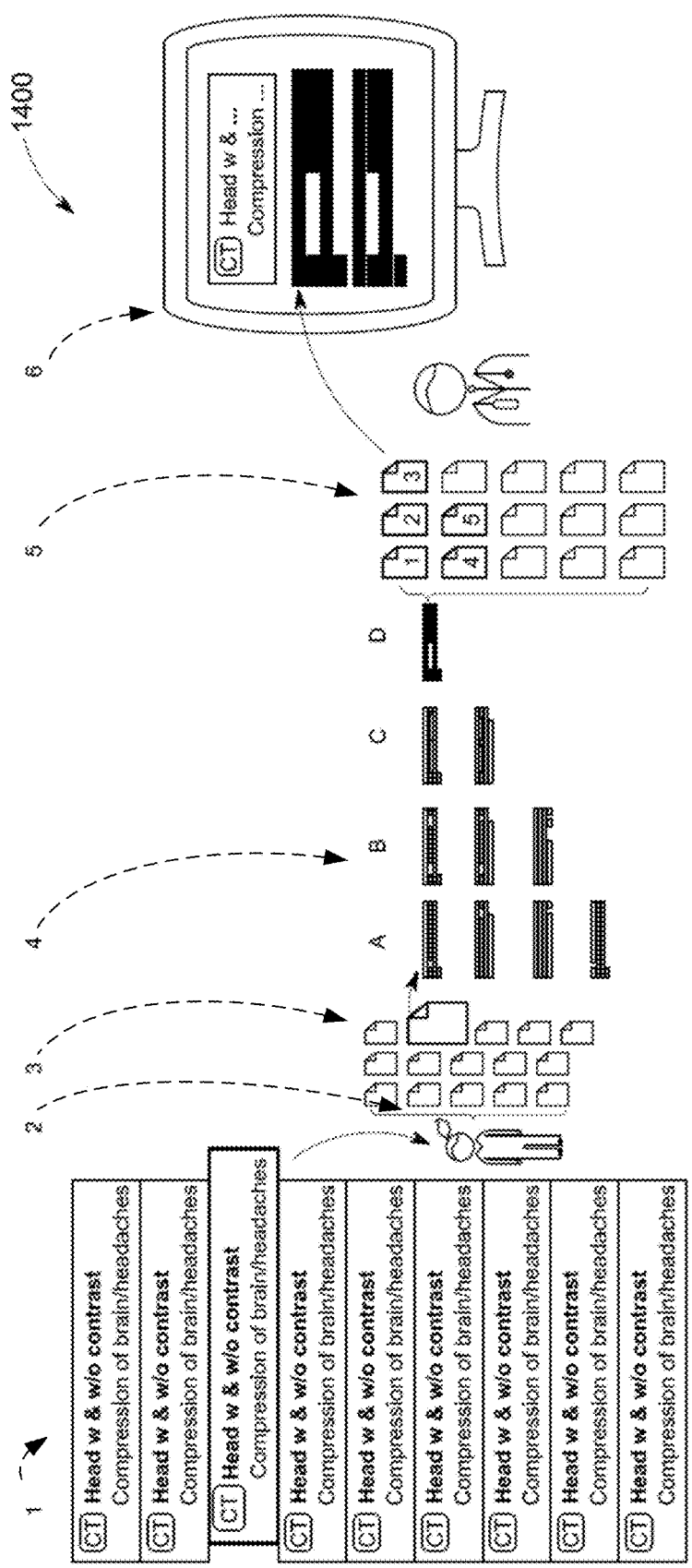
FIG. 14 illustrates an example process for relevancy analysis using natural language processing and artificial intelligence analysis of available documentation.

Flowcharts representative of example machine readable instructions for implementing and/or executing in conjunction with the example systems, algorithms, and interfaces of FIGS. 1-12 are shown in FIGS. 13-14. In these examples, the machine readable instructions comprise a program for execution by a processor such as the processor 1812 shown in the example processor platform 1800 discussed below in connection with FIG. 18. The program can be embodied in software stored on a tangible computer readable storage medium such as a CD-ROM, a floppy disk, a hard drive, a digital versatile disk (DVD), a BLU-RAY™ disk, or a memory associated with the processor 1812, but the entire program and/or parts thereof could alternatively be executed by a device other than the processor 1812 and/or embodied in firmware or dedicated hardware. Further, although the example program is described with reference to the flowcharts and/or processes illustrated in FIGS. 13-14, many other methods of implementing the examples disclosed and described here can alternatively be used. For example, the order of execution of the blocks can be changed, and/or some of the blocks described can be changed, eliminated, or combined.

As mentioned above, the example processes of FIG. 13-14 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 13-14 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 13 illustrates a flow diagram for an example method 1300 to evaluate medical information to provide relevancy and context for a given clinical scenario. At block 1302, a data event is received at a processor. The data event can be pushed and/or pulled from a data source to the data processor (e.g., an IRCC processor such as IRCC processor 404, data event consumer 510, etc.). For example, the data event can include receipt of a pipeline of documents and/or other data related to a patient and/or patient population triggered by selection of an exam from a worklist, etc.

At block 1304, receipt of the data event triggers processing of the data event by the processor. For example, when the data source listener 506 detects receipt of a data event from the data source 502, the listener 506 provides the data event in a queue 608 which triggers the data event consumer 510 to process the data event.

At block 1306, natural language processing is applied to the data event. For example, document data provided from a data source is processed using NLP techniques to generate structured data from the data event. Structured data can be used to form tags for terminology, concepts, other items, etc., to be flagged and/or emphasized in data and/or documents displayed and/or provided for further system processing by another component, for example.

At block 1308, the structured data is used to learn and determine similarity/dissimilarity and relevancy of the data to the given clinical scenario. For example, natural language processing and machine learning (e.g., by the machine, system, or processor) leverages prior patterns, history, habits, best practices, particular data, etc., to analyze similarity and/or dissimilarity of the data and relevance to the given clinical scenario as well as improve operation and interpretation for future analysis. At block 1308, data usage is also monitored to provide usage information for the data. For example, how frequently, how recently, how effectively, etc., user(s) (e.g., a current user, peer users, etc.) use the data being processed can be monitored and tabulated to form data usage statistics at a particular level (e.g., at a domain level, group level, individual level, etc.).

At block 1310, user preference information can be obtained to factor into data analysis. For example, users can indicate a preference for data through a rating system (e.g., like/like, relevant/irrelevant, thumbs up/thumbs down, stars, numerical rating, etc.).

At block 1312, data analysis, usage information, and/or preference information is provided to a relevancy algorithm to determine relevance of the data associated with the data event to the given clinical scenario. For example, domain and user usage, knowledge, preference, and workflow filters are applied to the gathered analysis and information to provide an indication (e.g., a score, a category, a range, a classification, etc.) of relevancy to the given clinical scenario (e.g., a foot x-ray, an abdominal ultrasound, dizziness, etc.). Thus, a collaborative filtering/recommendation information set can be provided through analysis of data and feedback from one or more users to determine relevancy (e.g., relevancy of clinical documents such as radiology reports, etc.).

At block 1314, an output is made available via an interface. For example, an output is made available to one or more external users (e.g., human, application, and/or system users, etc.) via an API, a graphical user interface, etc. Thus, in an example, document(s) associated with the data event along with analysis, contextual information, and a relevancy score can be provided via the interface.

Thus, information can be identified, retrieved, processed, and provided to help enrich and enlighten examination, diagnosis, and treatment of a patient in a collaborative, expansive, and evolutionary (e.g., learning) system. For example, a graphical user interface can be configured to dynamically accommodate both a diagnostic hub and workload manager and facilitate workload management as well as communication and collaboration among healthcare practitioners.

FIG. 14 illustrates an example process 1400 for relevancy analysis using natural language processing and artificial intelligence analysis of available documentation. At 1, pre-scheduled exams are reviewed prior to a scheduled scan. For example, at midnight and/or another time prior to start of a next day's shift, exams scheduled for the next day are reviewed. At 2, for each exam, an associated body part, modality, and reason for exam are identified and processed. At 3, a health information system, such as an EMR, EHR, PACS, RIS, EA, VNA, etc., is queried for clinical documents and/or other data related to patients having exams the next day.

At 4, most relevant paragraphs are identified and extracted from each document based on criteria including body part/region, modality, diagnosis, other linguistic feature(s) (e.g., relationship between body part and modality, reason for exam, etc.), etc. At 5, documents with a relevant paragraph are scored and ranked by how many matching features they contain and how clearly they match. At 6, when a radiologist opens an exam in the workflow manager, the radiologist sees the extracted content from the prioritized clinical notes. The extracts can be ordered according to Thus, with a patient and related clinical data as input, NLP with integrated medical dictionaries and an artificial neural network identifies an overlap in medical data such as signs and symptoms, diseases, etc., and outputs overlapping tagged concepts that are relevant to the study in context for the patient.

Figure 15:
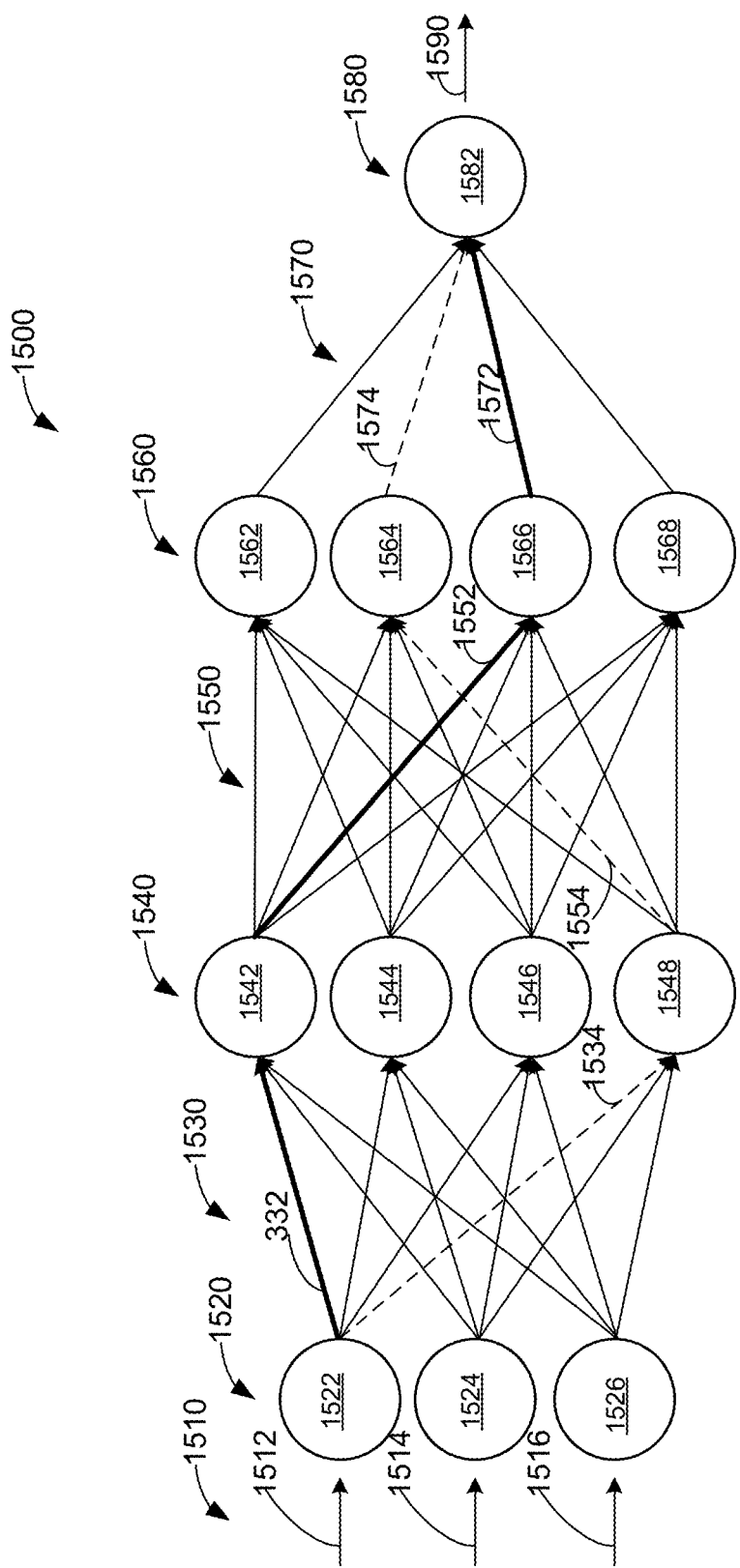
FIG. 15 illustrates an example artificial neural network that can be used to process document data and correlate with medical terminology information, reason for exam, and/or other patient particulars.

FIG. 15 illustrates an example convolutional neural network (CNN) that can be used in the AI 408 to process document data and correlate with medical terminology information, RFE, and/or other patient, user, and/or domain particulars, for example. FIG. 15 is a representation of an example learning neural network 1500. The example neural network 1500 includes layers 1520, 1540, 1560, and 1580. The layers 1520 and 1540 are connected with neural connections 1530. The layers 1540 and 1560 are connected with neural connections 1550. The layers 1560 and 1580 are connected with neural connections 1570. Data flows forward via inputs 1512, 1514, 1516 from the input layer 1520 to the output layer 1580 and to an output 1590.

The layer 1520 is an input layer that, in the example of FIG. 15, includes a plurality of nodes 1522, 1524, 1526. The layers 1540 and 1560 are hidden layers and include, the example of FIG. 15, nodes 1542, 1544, 1546, 1548, 1562, 1564, 1566, 1568. The neural network 1500 may include more or less hidden layers 1540 and 1560 than shown. The layer 1580 is an output layer and includes, in the example of FIG. 15, a node 1582 with an output 1590. Each input 1512-1516 corresponds to a node 1522-1526 of the input layer 1520, and each node 1522-1526 of the input layer 1520 has a connection 1530 to each node 1542-1548 of the hidden layer 1540. Each node 1542-1548 of the hidden layer 1540 has a connection 1550 to each node 1562-1568 of the hidden layer 1560. Each node 1562-1568 of the hidden layer 1560 has a connection 1570 to the output layer 1580. The output layer 1580 has an output 1590 to provide an output from the example neural network 1500.

Of connections 1530, 1550, and 1570 certain example connections 1532, 1552, 1572 may be given added weight while other example connections 1534, 1554, 1574 may be given less weight in the neural network 1500. Input nodes 1522-1526 are activated through receipt of input data via inputs 1512-1516, for example. Nodes 1542-1548 and 1562-1568 of hidden layers 1540 and 1560 are activated through the forward flow of data through the network 1500 via the connections 1530 and 1550, respectively. Node 1582 of the output layer 1580 is activated after data processed in hidden layers 1540 and 1560 is sent via connections 1570. When the output node 1582 of the output layer 1580 is activated, the node 1582 outputs an appropriate value based on processing accomplished in hidden layers 1540 and 1560 of the neural network 1500.

Thus, certain examples provide IRCC to deliver relevant patient context to radiologists when they are reviewing images. Example patient context includes surgical notes, pathology reports, and clinical notes, which are delivered directly to radiologists and embedded in their existing workflow. The IRCC apparatus 404 learns (e.g., using the example neural network model 1500, etc.) from radiologists via keywords and sentence structure how to select relevant clinical data.

In certain examples, the IRCC 404 processes and prioritizes a certain subset of documents to be displayed out of a large volume of documents available to the system 400. AI, image analysis, and document analysis are used to drive prioritization of documentation display and radiology worklist. In certain examples, the IRCC architecture 404 leverages data storage, an imaging interface, a scheduler, and a plurality of neural networks and/or other machine learning models to provide intelligent document selection and/or retrieval combined with NLP and concept tagging, as well as prioritization and scoring for the clinical context, to deliver relevant content with key terms and other information highlighted and/or otherwise emphasized for display and review by a radiologist and/or other user.

In certain examples, a cross-enterprise fabric ties a plurality of external systems, databases, etc., into one or more pipelines for delivery of content to the system 400 and its interface for processing and display. Documents, images, etc., come in from a plurality of systems and are formatted for a single input pipeline, which is processed with NLP and machine learning to identify and emphasize a certain subset of relevant results. For example, given the massive amount of data coming through the pipeline, too much data for any human to review, NLP can prepare the data and a machine learning model can be used to process the prepared data to identify relevant content (e.g., 85% of incoming data may be irrelevant to a particular reason for examination and/or other criterion for a patient to see a clinician, etc.). For example, RESTful endpoints and other data types can be converted (e.g., into Fast Healthcare Interoperability Resources (FHIR), Health Level Seven (HL7), Digital Imaging and Communications in Medicine (DICOM), etc.) and pumped into the relevancy processor 412 for relevancy processing.

Figure 16:
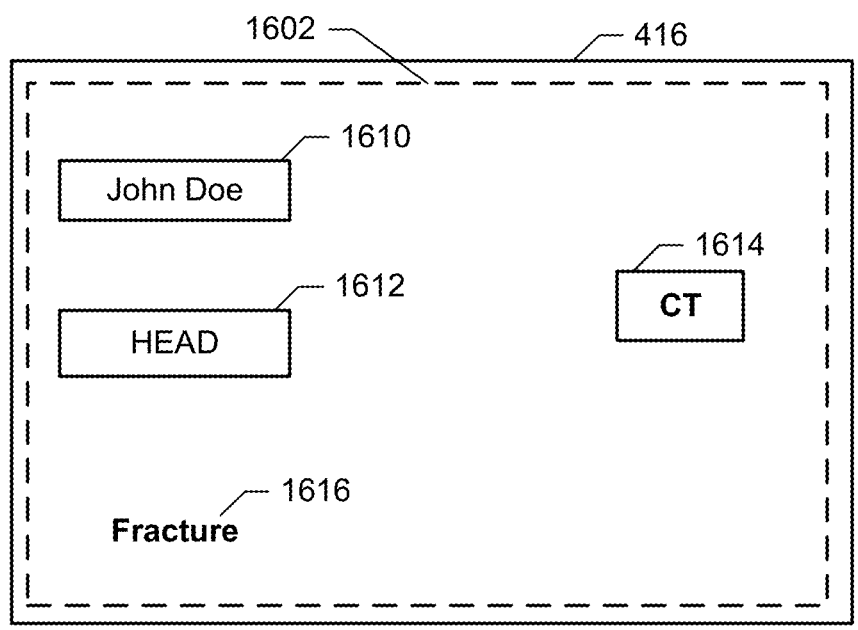
FIGS. 16-17 illustrate example displays of relevant documents via an example workflow manager after relevancy processing.

FIG. 16 illustrates an example implementation of the display 416, such as on the radiology desktop 720, etc., to convey context-sensitive, relevant results (and/or excerpts of results) via the workload manager and/or diagnostic hub (e.g., exam preview panel, patient library, comparison list, etc.), etc. Based on the relevancy analysis and processing of documents related to a particular patient, the interface 1602 shown on the example display 416 provides documents (e.g., in an exam preview, comparison panel, supplemental information display, other workspace of the diagnostic hub, etc.) with tagged terms, concepts, etc., emphasized 1610-1616 over the rest of the displayed document 1062. For example, tagged terms can be boxed, highlighted, bolded, elevated, shown in a different color, etc., so that they stand out from other surrounding information via the interface 1602.

Figure 17:
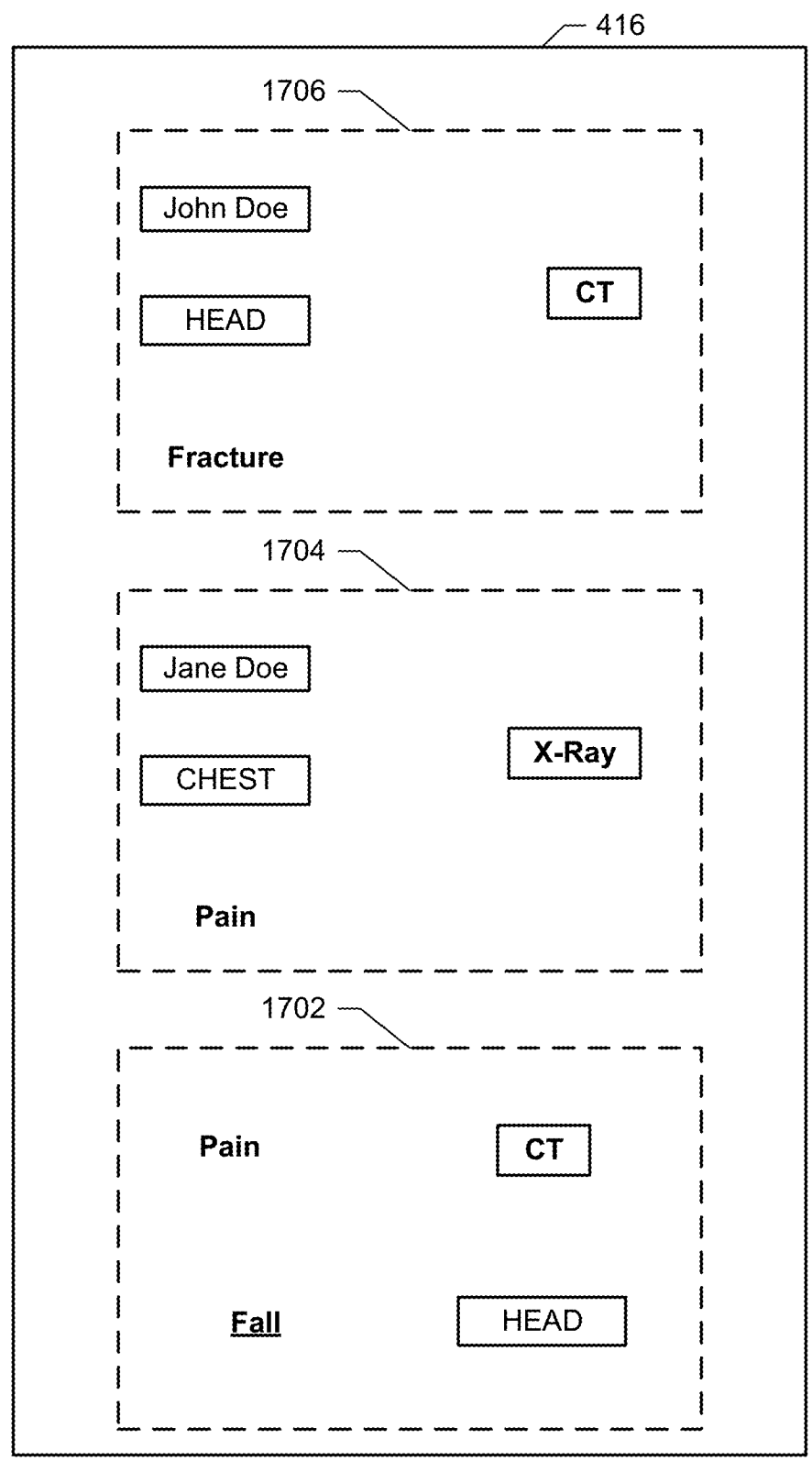

Thus, as shown in the example of FIG. 17, when a user at an imaging workstation 720 pulls up a patient record in preparation for an examination, the IRCC 404 and supporting system 400 delivers additional content (e.g., patient records, lab results, best practice documents, etc.) processed for relevancy and to highlight/emphasize/make prominent tagged key concepts, terms, items, etc., for expedited user review. For example, the display 416 of FIG. 17 shows a plurality of supporting documents 1702-1706 displayed for user interaction. For example, a user can drill down into and/or otherwise open one or more documents 1702-1706. The user can select a highlighted term to identify other corresponding highlighted terms in the documents 1702-1706, for example. In certain examples, the same tags are emphasized the same way in each document 1702-1706. In certain examples, documents 1702-1706 relevant to a particular clinical situation are made available via the interface display 416 based on the particular exam type, reason for exam, other clinical situation, user, patient, body part, modality, etc.

In certain examples, a user can input an additional criterion/term, such as a keyword or search term, etc., and that word or phrase, if found in the relevant document set 1702-1706, is highlighted in the applicable document(s) 1702-1706. In certain examples, a computer-aided diagnosis (CAD) system can automatically process tagged items in the documents 1702-1706 to assist with, recommend a next action, and/or make a diagnosis of a patient with an image and the supporting documents 1702-1706.

V. COMPUTING DEVICE

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 18:
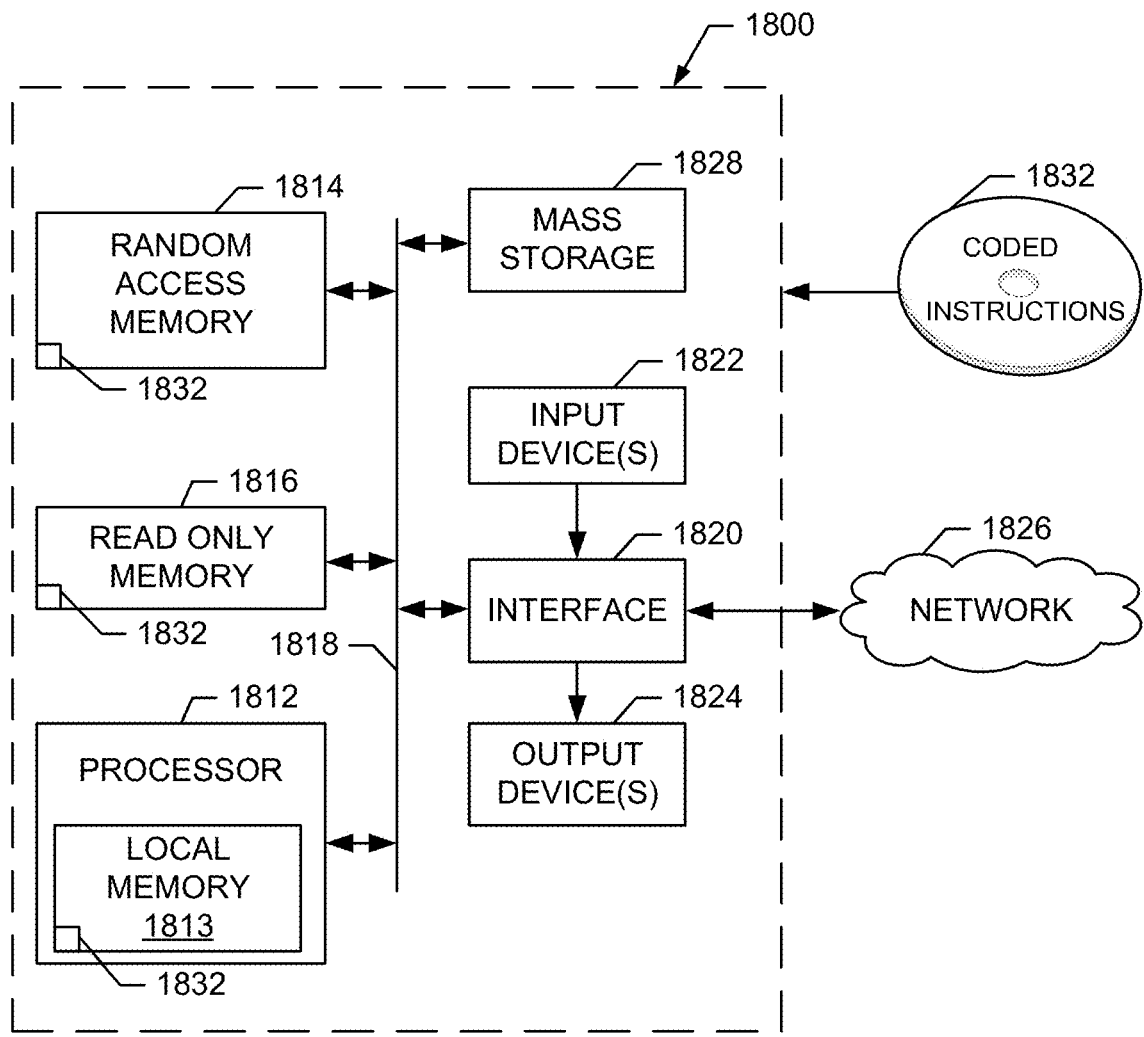
FIG. 18 shows a block diagram of an example processor system that can be used to implement systems and methods described herein.

FIG. 18 is a block diagram of an example processor platform 1800 capable of executing instructions to implement the example systems and methods disclosed and described herein. The processor platform 1800 can be, for example, a server, a personal computer, a mobile device (e.g., a cell phone, a smart phone, a tablet such as an IPAD™) a personal digital assistant (PDA), an Internet appliance, or any other type of computing device.

The processor platform 1800 of the illustrated example includes a processor 1812. The processor 1812 of the illustrated example is hardware. For example, the processor 1812 can be implemented by one or more integrated circuits, logic circuits, microprocessors or controllers from any desired family or manufacturer.

The processor 1812 of the illustrated example includes a local memory 1813 (e.g., a cache). The processor 1812 of the illustrated example is in communication with a main memory including a volatile memory 1814 and a non-volatile memory 1816 via a bus 1818. The volatile memory 1814 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1816 can be implemented by flash memory and/or any other desired type of memory device. Access to the main memory 1814, 1816 is controlled by a memory controller.

The processor platform 1800 of the illustrated example also includes an interface circuit 1820. The interface circuit 1820 can be implemented by any type of interface standard, such as an Ethernet interface, a universal serial bus (USB), and/or a PCI express interface.

In the illustrated example, one or more input devices 1822 are connected to the interface circuit 1820. The input device(s) 1822 permit(s) a user to enter data and commands into the processor 1812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1824 are also connected to the interface circuit 1820 of the illustrated example. The output devices 1824 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1820 of the illustrated example, thus, typically includes a graphics driver card, a graphics driver chip or a graphics driver processor.

The interface circuit 1820 of the illustrated example also includes a communication device such as a transmitter, a receiver, a transceiver, a modem and/or network interface card to facilitate exchange of data with external machines (e.g., computing devices of any kind) via a network 1826 (e.g., an Ethernet connection, a digital subscriber line (DSL), a telephone line, coaxial cable, a cellular telephone system, etc.).

The processor platform 1800 of the illustrated example also includes one or more mass storage devices 1828 for storing software and/or data. Examples of such mass storage devices 1828 include floppy disk drives, hard drive disks, compact disk drives, Blu-ray disk drives, RAID systems, and digital versatile disk (DVD) drives.

The coded instructions 1832 can be stored in the mass storage device 1828, in the volatile memory 1814, in the non-volatile memory 1816, and/or on a removable tangible computer readable storage medium such as a CD or DVD. The instructions 1832 can be executed by the processor 1812 to implement the IRCC processor 404, etc., as disclosed and described above.

VI. CONCLUSION

Thus, certain examples provide an event-based architecture generating more efficient data processing. In certain examples, natural language processing creates an easy to understand information hierarchy. In certain examples, an adaptable system can respond to multiple clinical environments. Faster display of information can lead to more efficient workflow.

Certain examples provide general schema that can be ported to a variety of databases. Certain examples further provide a user-friendly wizard to create worklist definitions. Worklist definitions can be ported among schema. Certain examples leverage an entity framework to provide functionality, collaboration, modules, and metadata management in an entity framework, for example. Worklists can be dynamically built and dynamically injected with context and user session information, for example.

Thus, certain examples provide a diagnostic cockpit that aggregates clinical data and artifacts. Certain examples facilitate determination of data relevancy factoring in patient, user, and study context. Certain examples provide diagnostic decision support through the integrated diagnostic cockpit.

Certain examples provide a dynamically adjustable interaction framework including both a workload manager and diagnostic hub accommodating a variety of worklists, exams, patients, comparisons, and outcomes. Certain examples improve operation of a graphical user interface and associated display and computer/processor through adaptive scalability, organization, and correlation.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost. Certain examples facilitate improved control over data. For example, certain example systems and methods enable care providers to access, view, manage, and manipulate a variety of data while streamlining workload management. Certain examples facilitate improved control over process. For example, certain example systems and methods provide improved visibility, control, flexibility, and management over workflow. Certain examples facilitate improved control over outcomes. For example, certain example systems and methods provide coordinated viewing, analysis, and reporting to drive more coordinated outcomes.

Certain examples leverage information technology infrastructure to standardize and centralize data across an organization. In certain examples, this includes accessing multiple systems from a single location, while allowing greater data consistency across the systems and users.

Technical effects of the subject matter described above can include, but are not limited to, providing systems and methods to enable an interaction and behavior framework to determine relevancy and recommend information for a given clinical scenario. Clinical workflow and analysis are dynamically driven based on available information, user preference, display configuration, etc. Moreover, the systems and methods of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging related clinical context apparatus comprising:
   a memory to store instructions and data; and
   at least one processor to at least:
      execute a scheduler to perform a prefetch operation for clinical data located in a plurality of documents residing in one or more connected systems; and
      analyze the plurality of documents to identify a subset of relevant documents in the plurality of documents by:
         applying natural language processing to identify terms in the plurality of documents, a subset of the identified terms forming tagged concepts;
         constructing a data structure of the tagged concepts;
         processing the identified terms using a machine learning model with respect to a relevancy criterion for an examination to select the subset of relevant documents, the machine learning model trained using at least radiologist usage patterns and keywords and deployed with the at least one processor to leverage the data structure of the tagged concepts to process the identified terms to select the subset of relevant documents;
         executing a gap analysis in real-time to select additional relevant documents for automated review, the gap analysis to identify, retrieve, and process, using the machine learning model, additional clinical data entered after the prefetch operation, wherein the additional clinical data indicates whether to administer a contrast agent to a patient, an environmental context for the examination, the environmental context comprising an inpatient, an outpatient, or an emergency department (ED) context, a disease category representing a neoplasm category, and a phase of treatment comprising a screening, a follow-up, a pre-surgery treatment, or a post-surgery treatment;
         modifying the subset of relevant documents by adding an emphasis to the tagged concepts found in the subset of relevant documents and the additional clinical data; and
      output the subset of relevant documents including emphasized tagged concepts.

2. The apparatus of claim 1, further including a communication interface to receive the plurality of documents from a plurality of data sources.

3. The apparatus of claim 1, wherein the relevancy criterion includes at least one of a body part, a modality, or a reason for the examination.

4. The apparatus of claim 1, wherein the machine learning model includes a deep learning network model.

5. The apparatus of claim 1, wherein the at least one processor is to output the subset of relevant documents by displaying the subset of relevant documents using a user interface for interaction.

6. The apparatus of claim 5, wherein the interaction includes updating the tagged concepts and emphasis of the tagged concepts in the subset of documents based on a term input using the user interface.

7. The apparatus of claim 1, further including a scheduler to retrieve the examination and trigger the analysis of the plurality of documents by looking ahead to a next schedule of examinations.

8. The apparatus of claim 1, further including a data source listener to listen for a data event to trigger the analysis of the plurality of documents.

9. The apparatus of claim 8, further including a data consumer to process the data event for the analysis of the plurality of documents.

10. The apparatus of claim 1, further comprising identifying domain model information indicating one or more entities and at least one relationship between the one or more entities, wherein the domain model information comprises a social history, a family history, a surgical history, or a combination thereof, and wherein the machine learning model is adapted based on a user model defined for each of the one or more entities.

11. The apparatus of claim 1, wherein the at least one processor is to create a table of the tagged concepts that are matched against the subset of relevant documents using a vector mapping matrix in the machine learning model.

12. A computer-readable storage medium including instructions which, when executed, cause at least one processor to at least:
   execute a scheduler to perform a prefetch operation for clinical data located in a plurality of documents residing in one or more connected systems; and
   analyze a plurality of documents to identify a subset of relevant documents in the plurality of documents by:
      applying natural language processing to identify terms in the plurality of documents, a subset of the identified terms forming tagged concepts;
      constructing a data structure of the tagged concepts;
      processing the identified terms using a machine learning model with respect to a relevancy criterion for an examination to select the subset of relevant documents, the machine learning model trained using at least radiologist usage patterns and keywords and deployed with the at least one processor to leverage the data structure of the tagged concepts to process the identified terms to select the subset of relevant documents;
      executing a gap analysis in real-time to select additional relevant documents for automated review, the gap analysis to identify, retrieve, and process, using the machine learning model, additional clinical data entered after the prefetch operation, wherein the additional clinical data indicates whether to administer a contrast agent to a patient, an environmental context for the examination, the environmental context comprising an inpatient, an outpatient, or an emergency department (ED) context, a disease category representing a neoplasm category, and a phase of treatment comprising a screening, a follow-up, a pre-surgery treatment, or a post-surgery treatment;
      modifying the subset of relevant documents by adding an emphasis to the tagged concepts found in the subset of relevant documents and the additional clinical data; and
      output the subset of relevant documents including emphasized tagged concepts.

13. The computer-readable storage medium of claim 12, wherein the relevancy criterion includes at least one of a body part, a modality, or a reason for examination.

14. The computer-readable storage medium of claim 12, wherein the machine learning model includes a deep learning network model.

15. The computer-readable storage medium of claim 12, wherein the at least one processor is to output the subset of relevant documents by displaying the subset of relevant documents using a user interface for interaction.

16. The computer-readable storage medium of claim 15, wherein the interaction includes updating the tagged concepts and emphasis of the tagged concepts in the subset of documents based on a term input using the user interface.

17. The computer-readable storage medium of claim 12, wherein the instructions, when executed, further cause the at least one processor to retrieve the examination and trigger the analysis of the plurality of documents by looking ahead to a next schedule of examinations.

18. A computer-implemented method comprising:
executing a scheduler to perform a prefetch operation for clinical data located in a plurality of documents residing in one or more connected systems; and
analyzing, by executing an instruction with a processor, a plurality of documents to identify a subset of relevant documents in the plurality of documents by:
applying natural language processing to identify terms in the plurality of documents, a subset of the identified terms forming tagged concepts;
constructing a data structure of the tagged concepts;
processing the identified terms using a machine learning model with respect to a relevancy criterion for an examination to select the subset of relevant documents, the machine learning model trained using at least radiologist usage patterns and keywords and deployed with the at least one processor to leverage the data structure of the tagged concepts to process the identified terms to select the subset of relevant documents;
executing a gap analysis in real-time to select additional relevant documents for automated review, the gap analysis to identify, retrieve, and process, using the machine learning model, additional clinical data entered after the prefetch operation, wherein the additional clinical data indicates whether to administer a contrast agent to a patient, an environmental context for the examination, the environmental context comprising an inpatient, an outpatient, or an emergency department (ED) context, a disease category representing a neoplasm category, and a phase of treatment comprising a screening, a follow-up, a pre-surgery treatment, or a post-surgery treatment;
modifying the subset of relevant documents by adding an emphasis to the tagged concepts found in the subset of relevant documents and the additional clinical data; and
outputting, by executing an instruction with the processor, the subset of relevant documents including emphasized tagged concepts.

19. The method of claim 18, wherein the relevancy criterion includes at least one of a body part, a modality, or a reason for the examination.

20. The method of claim 18, wherein outputting the subset of relevant documents includes displaying the subset of relevant documents using a user interface for interaction.

* * * * *